US006043415A

United States Patent [19]
Strizhov et al.

[11] Patent Number: 6,043,415
[45] Date of Patent: Mar. 28, 2000

[54] SYNTHETIC *BACILLUS THURINGIENSIS* CRYIC GENE ENCODING INSECT TOXIN

[75] Inventors: Nicolai Strizhov; Jeff Schell, both of Köln, Germany; Aviah Zilberstein, Doar Holon, Israel; Menachem Keller, Hadera, Israel; Baruch Sneh, Rehovot, Israel; Csaba Koncz, Köln, Germany

[73] Assignees: Ramot Univ. Auth. for Applied Research and Industrial Development Ltd., Ramat Aviv, Israel; Max-Planck-Gesellschaft Zur Forderung Der Wissenschaften e.V, Berlin, Germany

[21] Appl. No.: 08/771,986

[22] Filed: Dec. 23, 1996

Related U.S. Application Data

[60] Provisional application No. 60/027,896, Oct. 7, 1996.
[51] Int. Cl.$^7$ .............................. A01H 5/00; C12N 5/14; C12N 15/32; C12N 15/82
[52] U.S. Cl. .................................. 800/317.3; 435/320.1; 435/419; 536/23.71; 800/279; 800/302; 800/317.2; 800/317.4; 800/320.1; 800/322
[58] Field of Search ...................... 536/23.71; 435/172.3, 435/320.1, 419; 800/205, 250, DIG. 43, DIG. 42, DIG. 9, 279, 302, 317.3, 317.2, 317.4, 314, 322, 320.1

[56] References Cited

U.S. PATENT DOCUMENTS

| 5,126,133 | 6/1992 | Payne et al. | 424/93 L |
|---|---|---|---|
| 5,187,091 | 2/1993 | Donovan et al. | 435/240.4 |
| 5,188,960 | 2/1993 | Payne et al. | 435/252.3 |
| 5,246,852 | 9/1993 | Payne et al. | 435/252.31 |
| 5,254,852 | 10/1993 | De Greve et al. | 800/205 |
| 5,264,364 | 11/1993 | Donovan et al. | 435/252.5 |
| 5,322,687 | 6/1994 | Donovan et al. | 424/43 |
| 5,380,831 | 1/1995 | Adang et al. | 536/23.71 |
| 5,441,884 | 8/1995 | Baum | 435/252.31 |
| 5,500,365 | 3/1996 | Fischhoff et al. | 435/240.4 |
| 5,523,211 | 6/1996 | Pusztai-Carey et al. | 425/23 |
| 5,527,883 | 6/1996 | Thompson et al. | 530/350 |
| 5,556,784 | 9/1996 | Liu | 435/252.5 |
| 5,691,308 | 11/1997 | Payne et al. | 514/12 |
| 5,712,248 | 1/1998 | Kalman et al. | 514/12 |
| 5,792,928 | 8/1998 | Sanchis et al. | 800/205 |

FOREIGN PATENT DOCUMENTS

WO 90/06999  6/1990  European Pat. Off. .
0 400 246  12/1990  European Pat. Off. .

OTHER PUBLICATIONS

Vaeck M, et al. "Transgenic plants protected from insect attack." Nature 328: 33–37, Jul. 1987.
Honee G, et al. Nucleotide sequence of crystal protein gene isolated from *B. thuringiensis* subspecies entomocidus 60.5 coding for a toxin highly active Spodoptera species, 1988.

Van der Salm T, et al. Insect resistance of transgenic plants that express modified *Bacillus thuringiensis* crylA(b) and crylC genes: A resistance management strategy. Plant. Mol. Biol. 26: 51–59, 1994.

Höfte et al., "Insecticidal Crystal Proteins of *Bacillus thuringiensis*", *Microbiol. Rev.* 53(2) 242–255 (1989).

Aronson, "The Two faces of *Bacillus thuringiensis*: Insecticidal Proteins and Post–Expotential Survival", *Molecular Microbiology* 7(4): 489–496 (1993).

Schnepf, "*Bacillus thurigiensis* Toxins: Regulation, Activities and Structural Diversity", *Current Opinion in Biotechnology* 6(3): 305–312 (1995).

Vaeck et al., "Transgenic Plants Protected from Insect Attack", *Nature (Lond)* 328(6125): 33–37 (1987).

Burris et al., "Beet Armyworms (*Lepidoptera: Noctuidae*) in Northeast Louisiana: Observations on Uncommon Insect Pest", *Florida Entomologist* 77(4) 454–459 (1994).

Smith et al., "Mosquitocidal Activity of the CrylC Delta–entoxin from Bt subsp. *aizawai*", *Applied & Environ. Microbiol.* 62(2) 680–684 (1996).

Hill, D.S., Agricultural Insect Pests of the Tropics and Their Control, Cambridge University Press, Cambridge, UK 1983), p. 375.

Watson, Second Edition, Generation of Agriculturally Important Plants and Animals, (1992) pp. 473–475.

Honee et al., "Nucleotide Sequence of Crystal Protein Gene . . . Against Spodoptera species", *Nucleic Acids Research* 16(13): 6240 (1988).

Sanchis et al., "Nucleotide Sequence and Analysis of N–Terminal Coding Region . . . " *Molecular Microbiology* 3(2): 229–238 (1989).

D'Halluin et al., "Engineering of Herbicide–Resistant Alfalfa and Evaluation Under Field Conditions", *Crop Sci.* 30(4): 866–871 (1990).

*Primary Examiner*—Lynette R. F. Smith
*Assistant Examiner*—Amy J. Nelson
*Attorney, Agent, or Firm*—Foley & Lardner

[57] ABSTRACT

The present invention relates to a synthetic version of a gene isolated from *Bacillus thuringiensis* encoding an insectidical crystal protein designated CryIC, plants transformed with the gene, and the insecticidal crystal protein toxin expressed by the gene, all of which are used to control insects of the Spodoptera species as well as those of the Mamestra species.

11 Claims, 9 Drawing Sheets

1: AUTOMATED SYNTHESIS OF 5'-PHOSPHORYLATED OLIGONUCLEOTIDES

2: TEMPLATE DIRECTED LIGATION OF OLIGONUCLEOTIDES ANNEALED WITH A PARTIALLY COMPLEMENTARY SINGLE-STRANDED DNA CARRYING BACTERIAL *cryIC* SEQUENCES

30 - 60 TDL-CYCLES

*Pfu* ligase, rATP
MELTING (92°C, 1 min)
ANNEALING AND
LIGATION (52°C, 3 min)

3: SELECTIVE PCR AMPLIFICATION OF SYNTHETIC DNA STRAND

```
              -  AT    ATACA       TAAG       A        C    A
     GGATCCACCATGGAGGAGAACAATCAGAACCAGTGTATCCCTTACAATTGTCTTTCTAATCCTGAAGAAGTTCTTTTGGATGGAGAAAGGATCTCAACTG
   1 ----------+---------+---------+---------+---------+---------+---------+---------+---------+---------+
         M  E  E  N  N  Q  N  Q  C  I  P  Y  N  C  L  S  N  P  E  E  V  L  L  D  G  E  R  I  S  T  G

T  ▽  TT   G         TC  A      G        TTA       TA A TTA
     GTAACTCATCAATTGACATCTCTCTCTCACTTGTTCAGTTCTTGGTTTCTAACTTTGTGCCAGGAGGAGGATTCCTTGTTGGACTTATCGACTTCGTTTG
 101 ----------+---------+---------+---------+---------+---------+---------+---------+---------+---------+
         N  S  S  I  D  I  S  L  S  L  V  Q  F  L  V  S  N  F  V  P  G  G  G  F  L  V  G  L  I  D  F  V  W

A  C          ▽    AAAT  ATATT     A    AT
     GGGAATCGTTGGACCTTCTCAATGGGATGCATTTCTCGTTCAGATCGAACAGCTCATCAACGAAAGAATCGCTGAGTTCGCTAGGAATGCTGCTATTGCT
 201 ----------+---------+---------+---------+---------+---------+---------+---------+---------+---------+
         G  I  V  G  P  S  Q  W  D  A  F  L  V  Q  I  E  Q  L  I  N  E  R  I  A  E  F  A  R  N  A  A  I  A

TTA    TA     T   TAT   A  TA    ▽       TT              AT
     AACCTTGAAGGACTTGGAAACAACTTCAACATCTACGTGGAGGCATTCAAGGAATGGGAAGAAGATCCTAACAACCCAGCAACCAGGACCAGAGTGATCG
 301 ----------+---------+---------+---------+---------+---------+---------+---------+---------+---------+
         N  L  E  G  L  G  N  N  F  N  I  Y  V  E  A  F  K  E  W  E  E  D  P  N  N  P  A  T  R  T  R  V  I  D

CCT   A   CC T    G A              TCG  CAT    ▽    AC TAC   T       G
     ATAGGTTCCGTATCCTTGATGGACTTCTTGAAAGGGACATTCCTAGCTTTAGGATCTCTGGATTTGAAGTTCCACTTCTCTCTGTTTACGCTCAAGCTGC
 401 ----------+---------+---------+---------+---------+---------+---------+---------+---------+---------+
         R  F  R  I  L  D  G  L  L  E  R  D  I  P  S  F  R  I  S  G  F  E  V  P  L  L  S  V  Y  A  Q  A  A

C  G   A   ATA     ATT       ▽   GATCTA    TT    AT
     TAATCTCCATCTTGCTATCCTTAGAGATTCTGTGATCTTCGGAGAAAGATGGGGATTGACAACCATCAACGTGAACGAGAACTACAACAGACTCATCAGG
 501 ----------+---------+---------+---------+---------+---------+---------+---------+---------+---------+
         N  L  H  L  A  I  L  R  D  S  V  I  F  G  E  R  W  G  L  T  T  I  N  V  N  E  N  Y  N  R  L  I  R

TT    AT        ATGTTG  TAT TTAGA    G    ▽     A     TTT
     CACATCGATGAGTACGCTGATCACTGTGCTAACACTTACAACCGTGGACTCAACAACCTTCCTAAGTCTACCTATCAAGATTGGATCACATACAACCGAC
 601 ----------+---------+---------+---------+---------+---------+---------+---------+---------+---------+
         H  I  D  E  Y  A  D  H  C  A  N  T  Y  N  R  G  L  N  N  L  P  K  S  T  Y  Q  D  W  I  T  Y  N  R  L

AC   TA    ATA    C                                              ▽[HincII]A
     TTAGGAGAGACCTTACATTGACTGTTCTTGATATCGCTGCTTTCTTTCCAAACTATGACAATAGGAGATATCCAATTCAGCCAGTTGGTCAACTTACAAG
 701 ----------+---------+---------+---------+---------+---------+---------+---------+---------+---------+
         R  R  D  L  T  L  T  V  L  D  I  A  A  F  F  P  N  Y  D  N  R  R  Y  P  I  Q  P  V  G  Q  L  T  R TG   TATTTT    TA    A  ATA   TT          ▽    T
     GGAAGTTTACACTGACCCACTCATCAACTTCAACCCACAGCTTCAGTCTGTTGCTCAGCTTCCTACCTTCAACGTTATGGAGAGCAGCGCAATCAGAAAT
 801 ----------+---------+---------+---------+---------+---------+---------+---------+---------+---------+
         E  V  Y  T  D  P  L  I  N  F  N  P  Q  L  Q  S  V  A  Q  L  P  T  F  N  V  M  E  S  S  A  I  R  N TT A TTA   TT          G                   CTTT            AA
     CCTCACCTCTTTGACATCTTGAACAACCTTACAATCTTTACCGATTGGTTTAGTGTTGGACGTAACTTCTACTGGGGAGGACATCGAGTGATCTCTAGCC
 901 ----------+---------+---------+---------+---------+---------+---------+---------+---------+---------+
         P  H  L  F  D  I  L  N  N  L  T  I  F  T  D  W  F  S  V  G  R  N  F  Y  W  G  G  H  R  V  I  S  S  L T    A  ▽   A           AT         G             CT  TT   GAT    T
     TCATCGGAGGTGGTAACATCACATCTCCTATCTACGGAAGAGAGGCTAACCAGGAGCCTCCAAGATCATTCACTTTCAACGGACCTGTGTTCAGGACTCT
1001 ----------+---------+---------+---------+---------+---------+---------+---------+---------+---------+
         I  G  G  N  I  T  S  P  I  Y  G  R  E  A  N  Q  E  P  P  R  S  F  T  F  N  G  P  V  F  R  T  L A     TA TATA    ▽      G      T  TTA          AAT              T
     TTCAAATCCTACTCTTCGACTTCTTCAGCAACCTTGGCCAGCTCCACCATTCAACCTTCGTGGTGTTGAAGGAGTTGAGTTCTCTACACCTACAAACAGC
1101 ----------+---------+---------+---------+---------+---------+---------+---------+---------+---------+
         S  N  P  T  L  R  L  L  Q  Q  P  W  P  A  P  P  F  N  L  R  G  V  E  G  V  E  F  S  T  P  T  N  S
```

FIG. 2A

```
          T G     A  ▽  G           TA       TAG       T T              C       T        T A
     TTCACCTATCGTGGAAGAGGTACTGTTGATTCTCTTACTGAACTTCCACCTGAGGACAACAGTGTGCCACCTCGTGAAGGATACAGTCATCGTCTTTGTC
1201 ----------+---------+---------+---------+---------+---------+---------+---------+---------+---------+
      F T Y R G R G T V D S L T E L P P E D N S V P P R E G Y S H R L C H

T T       ▽ BglII ▽            TT A      A A T          G              ▽      A T
     ATGCAACCTTCGTTCAAAGATCTGGAACACCTTTCCTTACAACTGGTGTTGTGTTCTCTTGGACTCATCGTAGTGCAACTCTTACCAACACAATTGATCC
1301 ----------+---------+---------+---------+---------+---------+---------+---------+---------+---------+
      A T F V Q R S G T P F L T T G V V F S W T H R A T L T N T I D P

A T T A A  T A         T        G C    C        ▽     T           G
     AGAGAGGATCAACCAGATCCCTCTTGTGAAAGGATTCAGAGTTTGGGGAGGAACCTCTGTGATTACAGGACCAGGATTCACAGGAGGTGATATCCTTCGA
1401 ----------+---------+---------+---------+---------+---------+---------+---------+---------+---------+
      E R I N Q I P L V K G F R V W G G T S V I T G P F T G G D I L R

T         TT A     A     C TT T         T       ▽     T A           C
     AGAAACACCTTTGGTGACTTCGTTTCTCTTCAAGTGAACATCAACTCACCAATCACCCAAAGATACCGTCTTAGATTTCGTTACGCTTCTAGTAGGGATG
1501 ----------+---------+---------+---------+---------+---------+---------+---------+---------+---------+
      R N T F G D F V S L Q V N I N S P I T Q R Y R L R F R Y A S S R D A

A AT A       G      C      ▽    C           A T                    A A G       T
     CACGAGTTATCGTTCTTACAGGAGCTGCATCTACAGGAGTGGGAGGTCAAGTTAGTGTGAACATGCCTCTTCAGAAAACTATGGAGATCGGAGAGAACCT
1601 ----------+---------+---------+---------+---------+---------+---------+---------+---------+---------+
      R V I V L T G A A S T G V G G Q V S V N M P L Q K T M E I G E N L

A   ▽   T    T    TT           T  T             T A T G A              A T
     CACATCTAGAACATTCAGATACACCGACTTCAGTAATCCTTTCTCATTCAGAGCTAATCCAGACATCATCGGTATCAGTGAACAACCTCTCTTCGGTGCA
1701 ----------+---------+---------+---------+---------+---------+---------+---------+---------+---------+
      T S R T F R Y T D F S N P F S F R A N P D I I G I S E Q P L F G A

T      ▽       T A T A T A T T A                                 T T   A
     GGTTCTATCAGTAGCGGTGAACTTTACATCGACAAGATCGAGATCATCCTTGCAGATGCAACATTTGAAGCAGAATCTGACCTTGAAAGAGCACAAAAGT
1801 ----------+---------+---------+---------+---------+---------+---------+---------+---------+---------+
      G S I S S G E L Y I D K I E I I L A D A T F E A E S D L E R A Q K -

AGGATCC
1901 ------- 1907
```

FIG. 2B

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 1907 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 10..1899

(xi) SEQUENCE DESCRIPTION: SEQ ID NO:1:

```
GGATCCACC ATG GAG GAG AAC AAT CAG AAC CAG TGT ATC CCT TAC AAT         48
          Met Glu Glu Asn Asn Gln Asn Gln Cys Ile Pro Tyr Asn
            1               5                  10

TGT CTT TCT AAT CCT GAA GAA GTT CTT TTG GAT GGA GAA AGG ATC TCA       96
Cys Leu Ser Asn Pro Glu Glu Val Leu Leu Asp Gly Glu Arg Ile Ser
     15                  20                  25

ACT GGT AAC TCA TCA ATT GAC ATC TCT CTC TCA CTT GTT CAG TTC TTG      144
Thr Gly Asn Ser Ser Ile Asp Ile Ser Leu Ser Leu Val Gln Phe Leu
 30                  35                  40                  45

GTT TCT AAC TTT GTG CCA GGA GGA GGA TTC CTT GTT GGA CTT ATC GAC      192
```

-continued

| | | | |
|---|---|---|---|
| Val Ser Asn Phe Val Pro Gly Gly Phe Leu Val Gly Leu Ile Asp | | | |
| 50 55 60 | | | |
| TTC GTT TGG GGA ATC GTT GGA CCT TCT CAA TGG GAT GCA TTT CTC GTT | 240 | | |
| Phe Val Trp Gly Ile Val Gly Pro Ser Gln Trp Asp Ala Phe Leu Val | | | |
| 65 70 75 | | | |
| CAG ATC GAA CAG CTC ATC AAC GAA AGA ATC GCT GAG TTC GCT AGG AAT | 288 | | |
| Gln Ile Glu Gln Leu Ile Asn Glu Arg Ile Ala Glu Phe Ala Arg Asn | | | |
| 80 85 90 | | | |
| GCT GCT ATT GCT AAC CTT GAA GGA CTT GGA AAC AAC TTC AAC ATC TAC | 336 | | |
| Ala Ala Ile Ala Asn Leu Glu Gly Leu Gly Asn Asn Phe Asn Ile Tyr | | | |
| 95 100 105 | | | |
| GTG GAG GCA TTC AAG GAA TGG GAA GAA GAT CCT AAC AAC CCA GCA ACC | 384 | | |
| Val Glu Ala Phe Lys Glu Trp Glu Glu Asp Pro Asn Asn Pro Ala Thr | | | |
| 110 115 120 125 | | | |
| AGG ACC AGA GTG ATC GAT AGG TTC CGT ATC CTT GAT GGA CTT CTT GAA | 432 | | |
| Arg Thr Arg Val Ile Asp Arg Phe Arg Ile Leu Asp Gly Leu Leu Glu | | | |
| 130 135 140 | | | |
| AGG GAC ATT CCT AGC TTT AGG ATC TCT GGA TTT GAA GTT CCA CTT CTC | 480 | | |
| Arg Asp Ile Pro Ser Phe Arg Ile Ser Gly Phe Glu Val Pro Leu Leu | | | |
| 145 150 155 | | | |
| TCT GTT TAC GCT CAA GCT GCT AAT CTC CAT CTT GCT ATC CTT AGA GAT | 528 | | |
| Ser Val Tyr Ala Gln Ala Ala Asn Leu His Leu Ala Ile Leu Arg Asp | | | |
| 160 165 170 | | | |
| TCT GTG ATC TTC GGA GAA AGA TGG GGA TTG ACA ACC ATC AAC GTG AAC | 576 | | |
| Ser Val Ile Phe Gly Glu Arg Trp Gly Leu Thr Thr Ile Asn Val Asn | | | |
| 175 180 185 | | | |
| GAG AAC TAC AAC AGA CTC ATC AGG CAC ATC GAT GAG TAC GCT GAT CAC | 624 | | |
| Glu Asn Tyr Asn Arg Leu Ile Arg His Ile Asp Glu Tyr Ala Asp His | | | |
| 190 195 200 205 | | | |
| TGT GCT AAC ACT TAC AAC CGT GGA CTC AAC AAC CTT CCT AAG TCT ACC | 672 | | |
| Cys Ala Asn Thr Tyr Asn Arg Gly Leu Asn Asn Leu Pro Lys Ser Thr | | | |
| 210 215 220 | | | |
| TAT CAA GAT TGG ATC ACA TAC AAC CGA CTT AGG AGA GAC CTT ACA TTG | 720 | | |
| Tyr Gln Asp Trp Ile Thr Tyr Asn Arg Leu Arg Arg Asp Leu Thr Leu | | | |
| 225 230 235 | | | |
| ACT GTT CTT GAT ATC GCT GCT TTC TTT CCA AAC TAT GAC AAT AGG AGA | 768 | | |
| Thr Val Leu Asp Ile Ala Ala Phe Phe Pro Asn Tyr Asp Asn Arg Arg | | | |
| 240 245 250 | | | |
| TAT CCA ATT CAG CCA GTT GGT CAA CTT ACA AGG GAA GTT TAC ACT GAC | 816 | | |
| Tyr Pro Ile Gln Pro Val Gly Gln Leu Thr Arg Glu Val Tyr Thr Asp | | | |
| 255 260 265 | | | |
| CCA CTC ATC AAC TTC AAC CCA CAG CTT CAG TCT GTT GCT CAG CTT CCT | 864 | | |
| Pro Leu Ile Asn Phe Asn Pro Gln Leu Gln Ser Val Ala Gln Leu Pro | | | |
| 270 275 280 285 | | | |
| ACC TTC AAC GTT ATG GAG AGC AGC GCA ATC AGA AAT CCT CAC CTC TTC | 912 | | |
| Thr Phe Asn Val Met Glu Ser Ser Ala Ile Arg Asn Pro His Leu Phe | | | |
| 290 295 300 | | | |
| GAC ATC TTG AAC AAC CTT ACA ATC TTT ACC GAT TGG TTT AGT GTT GGA | 960 | | |
| Asp Ile Leu Asn Asn Leu Thr Ile Phe Thr Asp Trp Phe Ser Val Gly | | | |
| 305 310 315 | | | |
| CGT AAC TTC TAC TGG GGA GGA CAT CGA CTG ATC TCT AGC CTC ATC GGA | 1008 | | |
| Arg Asn Phe Tyr Trp Gly Gly His Arg Leu Ile Ser Ser Leu Ile Gly | | | |
| 320 325 330 | | | |
| GGT GGT AAC ATC ACA TCT CCT ATC TAC GGA AGA GAG GCT AAC CAG GAG | 1056 | | |
| Gly Gly Asn Ile Thr Ser Pro Ile Tyr Gly Arg Glu Ala Asn Gln Glu | | | |
| 335 340 345 | | | |
| CCT CCA AGA TCA TTC ACT TTC AAC GGA CCT GTG TTC AGG ACT CTT TCA | 1104 | | |
| Pro Pro Arg Ser Phe Thr Phe Asn Gly Pro Val Phe Arg Thr Leu Ser | | | |
| 350 355 360 365 | | | |
| AAT CCT ACT CTT CGA CTT CTT CAG CAA CCT TGG CCA GCT CCA CCA TTC | 1152 | | |

```
                Asn Pro Thr Leu Arg Leu Leu Gln Gln Pro Trp Pro Ala Pro Pro Phe
                                370                 375                 380

AAC CTT CGT GGT GTT GAA GGA GTT GAG TTC TCT ACA CCT ACA AAC AGC                  1200
Asn Leu Arg Gly Val Glu Gly Val Glu Phe Ser Thr Pro Thr Asn Ser
            385                 390                 395

TTC ACC TAT CGT GGA AGA GGT ACT GTT GAT TCT CTT ACT GAA CTT CCA                  1248
Phe Thr Tyr Arg Gly Arg Gly Thr Val Asp Ser Leu Thr Glu Leu Pro
        400                 405                 410

CCT GAG GAC AAC AGT GTG CCA CCT CGT GAA GGA TAC AGT CAT CGT CTT                  1296
Pro Glu Asp Asn Ser Val Pro Pro Arg Glu Gly Tyr Ser His Arg Leu
        415                 420                 425

TGT CAT GCA ACC TTC GTT CAA AGA TCT GGA ACA CCT TTC CTT ACA ACT                  1344
Cys His Ala Thr Phe Val Gln Arg Ser Gly Thr Pro Phe Leu Thr Thr
430                 435                 440                 445

GGT GTT GTG TTC TCT TGG ACT CAT CGT AGT GCA ACT CTT ACC AAC ACA                  1392
Gly Val Val Phe Ser Trp Thr His Arg Ser Ala Thr Leu Thr Asn Thr
            450                 455                 460

ATT GAT CCA GAG AGG ATC AAC CAG ATC CCT CTT GTG AAA GGA TTC AGA                  1440
Ile Asp Pro Glu Arg Ile Asn Gln Ile Pro Leu Val Lys Gly Phe Arg
        465                 470                 475

GTT TGG GGA GGA ACC TCT GTG ATT ACA GGA CCA GGA TTC ACA GGA GGT                  1488
Val Trp Gly Gly Thr Ser Val Ile Thr Gly Pro Gly Phe Thr Gly Gly
        480                 485                 490

GAT ATC CTT CGA AGA AAC ACC TTT GGT GAC TTC GTT TCT CTT CAA GTG                  1536
Asp Ile Leu Arg Arg Asn Thr Phe Gly Asp Phe Val Ser Leu Gln Val
        495                 500                 505

AAC ATC AAC TCA CCA ATC ACC CAA AGA TAC CGT CTT AGA TTT CGT TAC                  1584
Asn Ile Asn Ser Pro Ile Thr Gln Arg Tyr Arg Leu Arg Phe Arg Tyr
510                 515                 520                 525

GCT TCT AGT AGG GAT GCA CGA GTT ATC GTT CTT ACA GGA GCT GCA TCT                  1632
Ala Ser Ser Arg Asp Ala Arg Val Ile Val Leu Thr Gly Ala Ala Ser
            530                 535                 540

ACA GGA GTG GGA GGT CAA GTT AGT GTG AAC ATG CCT CTT CAG AAA ACT                  1680
Thr Gly Val Gly Gly Gln Val Ser Val Asn Met Pro Leu Gln Lys Thr
        545                 550                 555

ATG GAG ATC GGA GAG AAC CTC ACA TCT AGA ACA TTC AGA TAC ACC GAC                  1728
Met Glu Ile Gly Glu Asn Leu Thr Ser Arg Thr Phe Arg Tyr Thr Asp
        560                 565                 570

TTC AGT AAT CCT TTC TCA TTC AGA GCT AAT CCA GAC ATC ATC GGT ATC                  1776
Phe Ser Asn Pro Phe Ser Phe Arg Ala Asn Pro Asp Ile Ile Gly Ile
575                 580                 585

AGT GAA CAA CCT CTC TTC GGT GCA GGT TCT ATC AGT AGC GGT GAA CTT                  1824
Ser Glu Gln Pro Leu Phe Gly Ala Gly Ser Ile Ser Ser Gly Glu Leu
590                 595                 600                 605

TAC ATC GAC AAG ATC GAG ATC ATC CTT GCA GAT GCA ACA TTT GAA GCA                  1872
Tyr Ile Asp Lys Ile Glu Ile Ile Leu Ala Asp Ala Thr Phe Glu Ala
            610                 615                 620

GAA TCT GAC CTT GAA AGA GCA CAA AAG TAGGATCC                                     1907
Glu Ser Asp Leu Glu Arg Ala Gln Lys
        625                 630

(2) INFORMATION FOR SEQ ID NO:2:

(i) SEQUENCE CHARACTERISTICS:
        (A) LENGTH: 630 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Glu Asn Asn Gln Asn Gln Cys Ile Pro Tyr Asn Cys Leu Ser
```

-continued

```
  1               5                   10                  15
Asn Pro Glu Glu Val Leu Leu Asp Gly Glu Arg Ile Ser Thr Gly Asn
                 20                  25                  30

Ser Ser Ile Asp Ile Ser Leu Ser Leu Val Gln Phe Leu Val Ser Asn
             35                  40                  45

Phe Val Pro Gly Gly Gly Phe Leu Val Gly Leu Ile Asp Phe Val Trp
             50                  55                  60

Gly Ile Val Gly Pro Ser Gln Trp Asp Ala Phe Leu Val Gln Ile Glu
 65                  70                  75                  80

Gln Leu Ile Asn Glu Arg Ile Ala Glu Phe Ala Arg Asn Ala Ala Ile
                 85                  90                  95

Ala Asn Leu Glu Gly Leu Gly Asn Asn Phe Asn Ile Tyr Val Glu Ala
                100                 105                 110

Phe Lys Glu Trp Glu Glu Asp Pro Asn Asn Pro Ala Thr Arg Thr Arg
                115                 120                 125

Val Ile Asp Arg Phe Arg Ile Leu Asp Gly Leu Leu Glu Arg Asp Ile
130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
                180                 185                 190

Asn Arg Leu Ile Arg His Ile Asp Glu Tyr Ala Asp His Cys Ala Asn
                195                 200                 205

Thr Tyr Asn Arg Gly Leu Asn Asn Leu Pro Lys Ser Thr Tyr Gln Asp
210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
                260                 265                 270

Asn Phe Asn Pro Gln Leu Gln Ser Val Ala Gln Leu Pro Thr Phe Asn
                275                 280                 285

Val Met Glu Ser Ser Ala Ile Arg Asn Pro His Leu Phe Asp Ile Leu
                290                 295                 300

Asn Asn Leu Thr Ile Phe Thr Asp Trp Phe Ser Val Gly Arg Asn Phe
305                 310                 315                 320

Tyr Trp Gly Gly His Arg Leu Ile Ser Ser Leu Ile Gly Gly Gly Asn
                325                 330                 335

Ile Thr Ser Pro Ile Tyr Gly Arg Glu Ala Asn Gln Glu Pro Pro Arg
                340                 345                 350

Ser Phe Thr Phe Asn Gly Pro Val Phe Arg Thr Leu Ser Asn Pro Thr
                355                 360                 365

Leu Arg Leu Leu Gln Gln Pro Trp Pro Ala Pro Phe Asn Leu Arg
                370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
                420                 425                 430
```

```
Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
        450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
                500                 505                 510

Ser Pro Ile Thr Gln Arg Tyr Arg Leu Arg Phe Arg Tyr Ala Ser Ser
                515                 520                 525

Arg Asp Ala Arg Val Ile Val Leu Thr Gly Ala Ala Ser Thr Gly Val
                530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
                580                 585                 590

Pro Leu Phe Gly Ala Gly Ser Ile Ser Ser Gly Glu Leu Tyr Ile Asp
                595                 600                 605

Lys Ile Glu Ile Ile Leu Ala Asp Ala Thr Phe Glu Ala Glu Ser Asp
610                 615                 620

Leu Glu Arg Ala Gln Lys
625                 630

(2) INFORMATION FOR SEQ ID NO:3:

(i) SEQUENCE CHARACTERISTICS:
        (A) LENGTH: 1907 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGATCCACCA TGGAGGAAAA TAATCAAAAT CAATGCATAC CTTACAATTG TTTAAGTAAT      60

CCTGAAGAAG TACTTTTGGA TGGAGAACGG ATATCAACTG GTAATTCATC AATTGATATT     120

TCTCTGTCAC TTGTTCAGTT CTGGTATCTA ACTTTGTAC CAGGGGGAGG ATTTTTAGTT      180

GGATTAATAG ATTTTGTATG GGGAATAGTT GGCCCTTCTC AATGGGATGC ATTTCTAGTA     240

CAAATTGAAC AATTAATTAA TGAAAGAATA GCTGAATTTG CTAGGAATGC TGCTATTGCT     300

AATTTAGAAG GATTAGGAAA CAATTTCAAT ATATATGTGG AAGCATTTAA AGAATGGGAA     360

GAAGATCCTA ATAATCCAGC AACCAGGACC AGAGTAATTG ATCGCTTTCG TATACTTGAT     420

GGGCTACTTG AAAGGGACAT TCCTTCGTTT CGAATTTCTG GATTTGAAGT ACCCCTTTTA     480

TCCGTTTATG CTCAAGCGGC CAATCTGCAT CTAGCTATAT TAAGAGATTC TGTAATTTTT     540

GGAGAAAGAT GGGGATTGAC AACGATAAAT GTCAATGAAA ACTATAATAG ACTAATTAGG     600

CATATTGATG AATATGCTGA TCACTGTGCA AATACGTATA ATCGGGGATT AAATAATTTA     660

CCGAAATCTA CGTATCAAGA TTGGATAACA TATAATCGAT TACGGAGAGA CTTAACATTG     720

ACTGTATTAG ATATCGCCGC TTTCTTTCCA ACTATGACA ATAGGAGATA TCCAATTCAG      780

CCAGTTGGTC AACTAACAAG GGAAGTTTAT ACGGACCCAT TAATTAATTT TAATCCACAG     840
```

-continued

```
TTACAGTCTG TAGCTCAATT ACCTACTTTT AACGTTATGG AGAGCAGCGC AATTAGAAAT      900

CCTCATTTAT TTGATATATT GAATAATCTT ACAATCTTTA CGGATTGGTT TAGTGTTGGA      960

CGCAATTTTT ATTGGGGAGG ACATCGAGTA ATATCTAGCC TTATAGGAGG TGGTAACATA     1020

ACATCTCCTA TATATGGAAG AGAGGCGAAC CAGGAGCCTC CAAGATCCTT TACTTTTAAT     1080

GGACCGGTAT TTAGGACTTT ATCAAATCCT ACTTTACGAT TATTACAGCA ACCTTGGCCA     1140

GCGCCACCAT TTAATTTACG TGGTGTTGAA GGAGTAGAAT TTTCTACACC TACAAATAGC     1200

TTTACGTATC GAGGAAGAGG TACGGTTGAT TCTTTAACTG AATTACCGCC TGAGGATAAT     1260

AGTGTGCCAC CTCGCGAAGG ATATAGTCAT CGTTTATGTC ATGCAACTTT TGTTCAAAGA     1320

TCTGGAACAC CTTTTTTAAC AACTGGTGTA GTATTTTCTT GGACGCATCG TAGTGCAACT     1380

CTTACAAATA CAATTGATCC AGAGAGAATT AATCAAATAC CTTTAGTGAA AGGATTTAGA     1440

GTTTGGGGGG GCACCTCTGT CATTACAGGA CCAGGATTTA CAGGAGGGGA TATCCTTCGA     1500

AGAAATACCT TTGGTGATTT TGTATCTCTA CAAGTCAATA TTAATTCACC AATTACCCAA     1560

AGATACCGTT TAAGATTTCG TTACGCTTCC AGTAGGGATG CACGAGTTAT AGTATTAACA     1620

GGAGCGGCAT CCACAGGAGT GGGAGGCCAA GTTAGTGTAA ATATGCCTCT TCAGAAAACT     1680

ATGGAAATAG GGAGAACTT AACATCTAGA ACATTTAGAT ATACCGATTT TAGTAATCCT      1740

TTTTCATTTA GAGCTAATCC AGATATAATT GGGATAAGTG AACAACCTCT ATTTGGTGCA     1800

GGTTCTATTA GTAGCGGTGA ACTTTATATA GATAAAATTG AAATTATTCT AGCAGATGCA     1860

ACATTTGAAG CAGAATCTGA TTTAGAAAGA GCACAAAAGT AGGATCC                   1907
```

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

```
AAGAGGATCC ACCATGGAGG AGAAC                                             25
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

```
ATGATCTAGA TGCAGTAGCG                                                   20
```

(2) INFORMATION FOR SEQ ID NO:6:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

GTCAACTAAC AAGGGAAGTT TATACGGACC CACGCTACTG CATCTAGATC AT                52

(2) INFORMATION FOR SEQ ID NO:7:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

GATAACTCGA GCGAGCCTAA ACTATGACAA TAGGAGATAT CCAATTCAGC CCAGTTG         57

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

GATAACTCGA GCGAGCCTA                                                    19

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

CCTGACTCTA GAAGATC                                                      17

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

CTGTCTGAAT TCAAAGATC                                                    19

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

-continued (xi) SEQUENCE DESCRIPTION: SEQ ID NO:11:

AGCATGCGGC CGCGGATCC                                                19

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

GATCTGCGGC CGCA                                                     14

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Trp Pro Ala Pro Pro Phe Asn
1               5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Cys Gln Arg His His Phe Asn
1               5

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

Gln Pro Trp Pro

SYNTHETIC *BACILLUS THURINGIENSIS* CRYIC GENE ENCODING INSECT TOXIN

This application claims priority to provisional application Ser. No. 60/027,896, filed Oct. 7, 1996, which is incorporated herein by reference.

FIELD OF THE INVENTION

The present invention relates to a synthetic version of a gene isolated from *Bacillus thuringiensis* (hereinafter "*Bt*" or "*B. thuringiensis*") encoding an insecticidal crystal protein designated CryIC, plants transformed with the gene, and the insecticidal crystal protein toxin expressed by the gene, all of which are used to control insects of the Spodoptera species as well as those of the Mamestra species.

BACKGROUND OF THE INVENTION

Insect infestation is responsible for millions of dollars of losses to commercially valuable agricultural crops each year. More than three billion dollars is spent worldwide annually to control insect pests. Traditionally, crops have been controlled from insect pests primarily through the use of toxic sprays. Unfortunately, residues of the sprays remaining on the fruits and vegetables have accumulated in human tissues, often with adverse effects, while at the same time many insects have become immune or resistant to the toxins. Additionally, the sprays often kill useful organisms, and precipitation runoff washes the toxins into streams and other bodies of water often killing fish.

Because of these and other disadvantages of using toxic sprays, alternative means of crop protection have been developed. One approach is the use of biological pesticides. One such agent is the bacteria *B. thuringiensis* which has been very effective against a variety of caterpillars and worms. This bacterium has been traditionally sold in the form of a dust containing millions of spores. When the spores are sprayed on plants, they are harmless to humans and animals other than the target insect. During its sporulation cycle, *Bt* produces proteins toxic to certain pests in crystal form known as crystal delta-endotoxins. When the insect ingests any plant tissue with *Bt* spores on it, *Bt* δ-endotoxin quickly becomes active within the insect's digestive tract, soon paralyzing the gut. The insect stops feeding within two or three hours.

The delta-endotoxin are encoded by crystal protein ("cry") genes. Thus far, over 100 Cry proteins were identified and classified according to their sequence homology and insect specificity (reviewed in Höfte and Whiteley, 1989; Aronson 1993, Schnepf 1995). The cry genes have been divided into six classes and several subclasses based on structural similarities and insecticidal specificity. The major classes are as follows:

| Class  | Insect Specificity                        |
| ------ | ----------------------------------------- |
| cryI   | Lepidoptera (butterflies, moths)          |
| cryII  | Lepidoptera and Diptera (flies, mosquitos)|
| cryIII | Coleoptera (beetles, weevils)             |
| cryIV  | Diptera (flies, mosquitos)                |
| cryV   | Coleoptera and Lepidoptera                |
| cryVI  | Nematode (roundworms)                     |

With particular regard to the lepidoptera-specific crystal proteins (CryI), to which the present invention is directed, six subclasses having different gene types have been identified. Subclasses of the cryI genes include the following: cryIA (a), cryIA (b), cryIA (c), cryIB, cryIC, and cryID and others. CryIC endotoxin is the most active *B. thuringiensis* crystal protein against the Spodoptera species which includes the following pests: *S. littoralis, S. exempta, S. exigua, S. frugiperda, S. litura* and others.

Unfortunately, production of the bacterial spores for commercial use is limited and the protective effect is short-lived. Accordingly, plant molecular biologists have developed transgenic plants that express the *Bt* toxin within their cells and tissues which have been effective against pests which feed on the leaves of the plant. For example, U.S. Pat. No. 5,187,091 to Donovan et al. describes incorporating into a plant a cryIIIC gene thereby rendering the plant more resistant to insect attack. Additionally, tobacco and tomato plants expressing the *Bt* toxin gene reportedly have killed larvae of tobacco hornworms. However, the wild-type crystal gene is poorly expressed in transgenic plants. Hence, protection is not attained against less sensitive, but agronomically important, insect pests like the cotton bollworms. (Watson et al. Recombinant DNA, 2d ed. 1992). The expression of the full-length lepidopteran specific *Bt* gene (cryI) in particular has been reported to be unsuccessful in expressing insecticide in some plants. (Vaeck et al., 1987)

To increase expression in plants, truncated and synthetic genes containing codons preferred in plants have been successfully employed.

U.S. Pat. No. 5,380,831 to Adang et al. discloses a synthetic *B. thuringiensis* gene designed to be expressed in plants at a level higher than naturally occurring *Bt* genes. The gene utilizes codons preferred in plants. The modifications described include the elimination of CUUCGG hairpins and plant polyadenylation signals and modifying the A+T content to that found in plants.

U.S. Pat. No. 5,500,365 to Fischoff et al. discloses synthetic plant genes which encode insecticidal proteins of *Bt* for plant transformation wherein the genes express their protein product at higher levels than the wild-type genes. In particular, they removed regions with many consecutive A+T bases or G+C bases as well as ATTTA sequences and putative polyadenylation signals, and the condon usage was changed according to plant preferences.

The insecticidal spectrum of *Bt* thus far expressed in transgenic plants is limited. Genes encoding the processed forms of CryIA(a), (b) and (c) have been expressed in plant-associated bacteria and transgenic plants to control major insect pests of maize, rice, cotton, tomato, potato and tobacco. Nonetheless, insects of the Spodoptera species, which cause severe agricultural damage, have thus far escaped efficient control because of problems preventing a high level expression of CryIC toxins in transgenic plants. Therefore, the engineering of *Bt* toxins with novel specificity is essential for the biological control of recalcitrant plague insects, such as Spodoptera. Members of the Spodoptera genus feed on over 40 different plant families world-wide, including at least 87 species of economic importance. Armyworms, most of which fall within the genus Spodoptera, march in swarms from field to field devastatingly defoliating entire crops. In the United States corn, sorghum and peanut are crops upon which fall armyworm (*Spodoptera frugiperda*) infestations often reach devastating levels. In one year, for example, losses in the state of Georgia alone were estimated at over 20 million dollars. Corn yield losses attributed to the fall armyworm for the United States have been estimated at 2% annually. In the southeastern United States, *S. frugiperda*, is a major pest of corn, sorghum and peanut, causing more than $60 million in damages per year. From the various insecticidal crystal proteins of B. thuringiensis expressed in transgenic plants that have been disclosed in prior art none showed activity required for plant protection against Spodoptera species. Moreover, no significant differences in leaf area consumed, mortality or pupal weights of S. exigua larvae were detected between transgenic B. thuringiensis Monsanto cotton line and non-transformed plants (Burns et al., 1994).

The Spodoptera species are polyphagous cutworms and armyworms, that may amplify to enormous numbers and devastate huge agricultural areas. The wide-spread beet armyworm S. exigua attacks rice, sugarbeet, alfalfa, cotton, corn, tobacco, tomato, potato, onions, peas, citrus, sunflower, and many grasses. The Egyptian cotton leafworm S. littoralis, a major pest in African and Mediterranean countries, favors fodder crops, such as alfalfa and clover, but also feeds on many vegetables, industrial crops, medical plants, ornamentals, and trees. Young Spodoptera larvae may be controlled by pyrethroids, DDT, chlorinated hydrocarbons and organophosphorous insecticides. However, because the eggs are laid on grassland, the efficiency of chemical insecticides, including the most efficient compounds methomyl and Pirate (AC303630), is rather limited. During the last decades a considerable effort was therefore invested into the development of safe insecticides to control armyworms in an environmentally friendly fashion.

Despite the significant damage caused by Spodoptera insects, safe and efficient pest control through the genetic engineering of plants is lacking because of the difficulty of achieving a high level of expression of CryIC toxin in transgenic plants. It would therefore be most desirable to have a gene encoding CryIC toxin that can be expressed in transgenic plants thereby safeguarding them against Spodoptera pests in an effective yet environmentally friendly manner.

SUMMARY OF THE INVENTION

The present invention relates to a synthetic Bt gene that expresses CryIC delta-endotoxins against Spodoptera insects when expressed in plants transfected by the gene. More specifically, it comprises a chemically synthesized gene coding for a truncated CryIC protoxin of 630 amino acids which has been expressed in alfalfa, tobacco, and potato plants and has proven to provide resistance to S. littoralis and S. exigua.

To improve the engineering of CryIC toxins, the gene according to the present invention establishes a consensus CryIC sequence within the boundaries of the entomocidal fragment of CryIC toxin that confers resistance to midgut proteases and larvae of Spodoptera littoralis. Insecticidal Cry proteins, produced as protoxins (65–140 kDa) in parasporal crystals of Bacillus thuringiensis (Bt), are active as selective entomocidal agents. The crystalline Bt protoxins are solubilized and activated in the midgut of insects of proteolysis. The activated toxins (60–70 kDa) bind to the membrane of midgut columnar cells and form ion-channels, inducing osmotic lysis of the epithelium. Engineering of insects resistance in maize, rice, cotton, tomato, potato, and tobacco shows that a significant modification of the bacterial cry coding sequences is essential to express these Bt toxin genes in plants.

Various features of the natural Bt genes differ from those of plants and heterologous genes expressed in plants. Bt genes are rich in adenine (A) and thymine (T) (more than 62%) while plant exons have about 45%–55% A+T content. Fortuitous plant processing signals present in Bt genes drastically diminish the level of their expression in plant cells. Efficient transcription of the synthetic cryIC gene according to the present invention in plant cell nuclei was achieved by the removal of AT rich sequences that may cause mRNA instability or aberrant splicing, and the translation of cry mRNAs is enhanced by modification of their codon usage to make it more similar to that of the host plant. In addition, the sequence context around the translation start was modified to conform to the eukaryotic consensus.

Synthesis of the synthetic gene herein was accomplished using a unique method "TDL-PCR" described herein and in more detail in our co-pending U.S. application which is incorporated herein by reference.

The synthetic gene according to the present invention may be employed to transform most plants thereby protecting them against pests which are members of the Spodoptera genus (Lepidoptera, Noctuidae) which feed on over 40 different plant families world-wide, including at least 87 species of economic importance (Hill, 1983). For example, the widespread beet armyworm S. exigua attacks rice, sugarbeet, alfalfa, cotton, corn, tobacco, tomato, potato, onions, peas, citrus, sunflower, and many grasses. The Egyptian cotton leafworm S. littoralis, a major pest in African and Mediterranean countries, favors fodder crops, such as alfalfa and clover, but also feeds on many vegetables, industrial crops, medical plants, ornamentals, and trees.

Additionally, the CyIC toxin that is expressed by transgenic plants according to the present invention can be collected and used, for example, as an insecticidal spray due to the fact that the protein is water soluble. CryIC toxins produced by bacteria, in contrast, are water insoluble rendering them undesirable for a variety of industrial and agricultural applications.

With the foregoing and other objects, advantages and features of the invention that will become hereinafter apparent, the nature of the invention may be more clearly understood by reference to the following detailed description of the invention, the figures, and the appended claims.

(A) neonate larvae of S. littoralis reared on transgenic (bottom) and non-transformed (top) alfalfa (M. sativa) plants.

(B) "free choice" bioassays with leaves from transgenic (right) and nontransgenic (left) alfalfa plants and larvae of S. exigua (3rd instar).

(C–D) leaf (C-from tobacco; D-from alfalfa) bioassays with 5th instar larvae of S. exigua reared on leaves taken from transgenic (right) and nontransgenic (left) plants.

(E) bioassays with alfalfa soil grown transgenic (left) and non-transgenic (right) plants and larvae of S. exigua.

Figure 5:
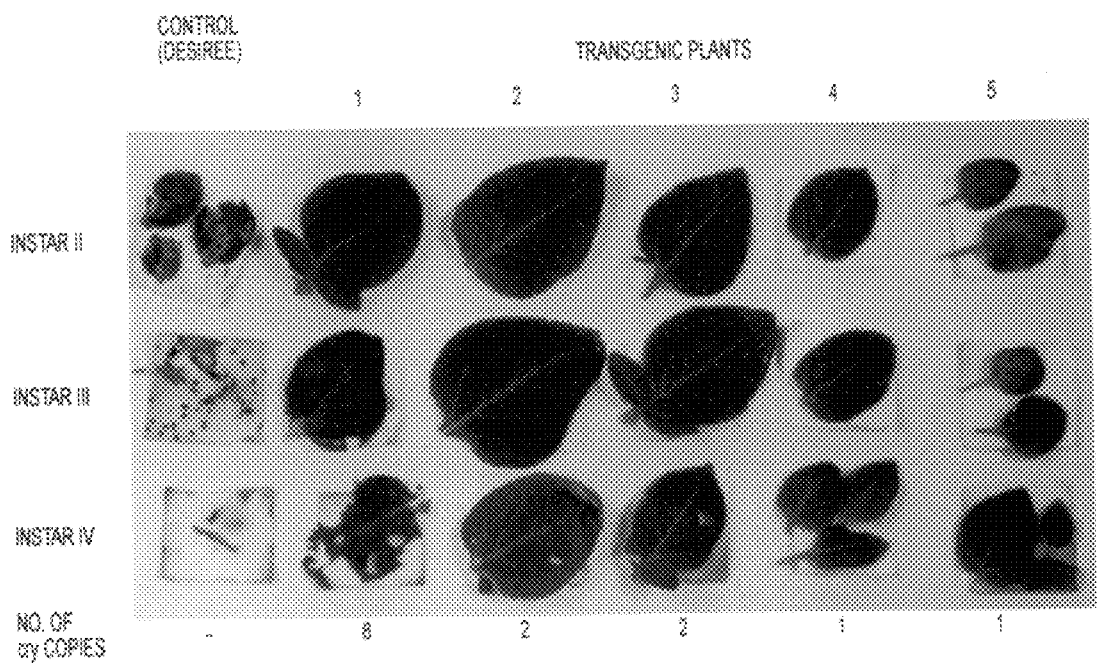

FIG. 5 is a bioassay of transformed potato plants (Desiree). Spodoptera littoralis larvae of the 2nd to 4th instars were fed on leaves of Desiree (control) and primary transformants. 1-plant No. AR1(2), 2-plant No. AR1(1), 3-plant No. AR1(3), 4-plant No. AR1(5), 5-plant AR1 (6). Leaves were photographed 48 h after being exposed to the larvae.

Figures 1, 6A:
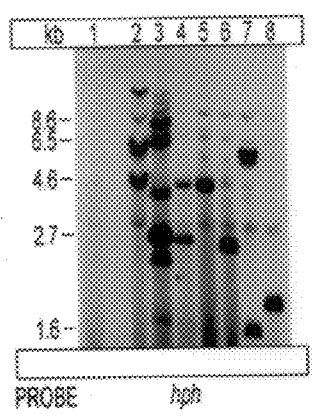
Figures 2, 6A:
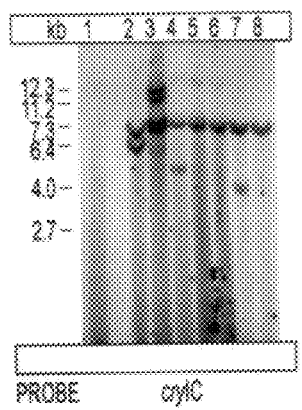
FIG. 2 shows the nucleotide sequence of the synthetic cryIC gene (SEQ ID NO:1). Where different, the native (bacterial) sequence is shown above (SEQ ID NO:3). The amino acid sequence is shown below (SEQ ID NO:2).
Figures 3, 6A:
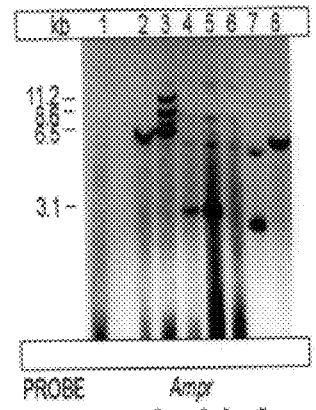
Figures 1, 6B:
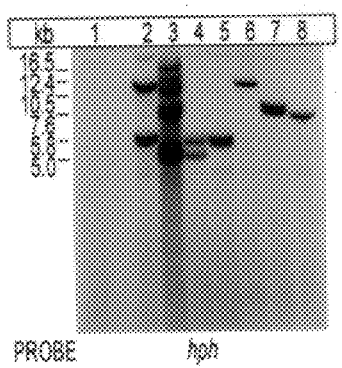
Figures 2, 6B:
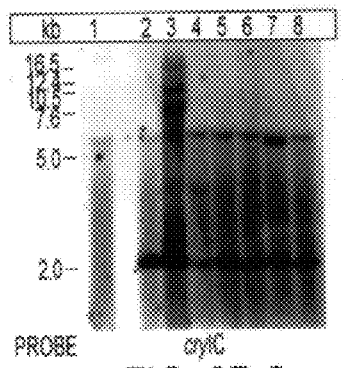
Figures 3, 6B:
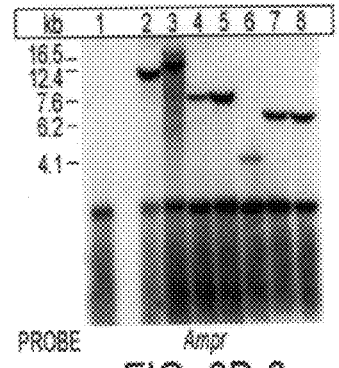

FIGS. 6A–6B is a Southern blot analysis which confirms the integration of the cryIC gene into plant genome. Plant DNA (20 µg) was digested with the restriction enzyme EcoRI in panel A and XbaI in panel B and electrophoresed on 0.8% agarose TAE gels. DNA was then transferred onto nylon membranes and probed with $^{32}$P labeled hph (a), cryIC(b) and with Amp resistance gene (c). Lane 1—control Desiree plant, lanes 2–8 transformed potato plants No. 1,2,3,5,6,7,8 carrying 2, >8, 2,1,1,3 and 1 copies of the cryIC gene respectively. Partial digestion with XbaI (which is sensitive to methylation) of plant DNA extracted from potato plant carrying at least 8 copies of the synthetic cryIC gene (panel B, lane 3), suggests possible involvement of plant hyper-methylation.

Figure 7:
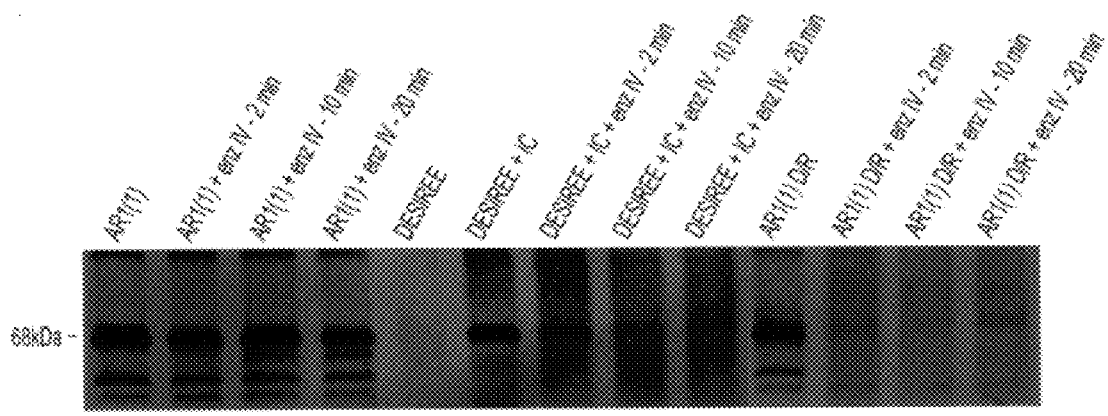

FIG. 7 is a Western blot analysis of total proteins extracted from the transgenic plant AR1(1) and incubated in vitro with gut proteases from 4th instar larvae. Similar AR1(1) protein samples were subjected to sequential denaturation and renaturation (D/R) which completely abolished their resistance to proteolysis (last mixed with 10 ng E. coli produced CryIC (630aa) were incubated with gut proteases. No resistance of bacterial CryIC to proteases was observed. Following incubation the protein samples were separated on 12% SDS-acrylamide gel, blotted onto PVDF membrane and probed with ani-CryIC polyclonal antibodies.

From left to right:

| | |
|---|---|
| Lane 1 | AR1(1) proteins, no gut proteases. |
| Lane 2–4 | AR1(1) proteins incubated with gut proteases (0.2 µg proteins, depicted as enzIV) for 2, 10 and 20 min. respectively. |
| Lane 5 | Proteins of non-transformed Desiree plant. |
| Lane 6 | Proteins of non-transformed Desiree plant mixed with 10 ng E. coli produced CryIC (630aa). |
| Lane 7–9 | as in 6 but incubated with gut proteases for 1, 10 and 20 min. respectively. |
| Lane 10 | AR1(1) proteins after denaturation and renaturation as detailed below. |
| Lane 11–13 | AR1(1) proteins subjected to 6M Guanidinium hydrochloride (denaturation), dialyzed against 50 mM Tris-HCI, pH8 over-night (renaturation) and then incubated with gut proteases for 2, 10 and 20 min. respectively. |

DETAILED DESCRIPTION OF THE INVENTION

The process for gene synthesis is described in detail in Example I and is described in even greater detail in our co-pending U.S. application Ser. No. 08/769,802 entitled "Gene Synthesis Method" filed on Dec. 20, 1996, which is incorporated herein by reference. In short, chemically synthesized and phosphorylated oligonucleotides of the gene to be created are assembled on a single-stranded partially homologous template DNA derived from the natural or wild-type gene. After annealing, the nicks between adjacent oligonucleotides are closed by a thermostable DNA ligase followed by repeated cycles of melting, annealing, and ligation. This template directed ligation ("TDL") results in a new single-stranded synthetic DNA product which is subsequently amplified and isolated from the wild type-template strand by the polymerase chain reaction (PCR) with short flanking primers that are complementary only to the new synthetic strand. These PCR end-primers contain suitable restriction cleavage sites for cloning of the synthetic double-stranded DNA fragments. This process is illustrated schematically in FIG. 1.

Although the gene according to the present invention was used to successfully transform alfalfa, Arabidopsis, tobacco and potato plants, it can be used to transform any other dicot in a similar manner so as to render the plant resistant to insect attack. Genetic engineering of plants with the cryIC gene (FIG. 2) may be accomplished by introducing a vector containing the gene into the plant cells using one of a variety of vectors known to those in the plant genetic engineering art. The synthetic cryIC gene according to the present invention may be delivered into the plant cells by Agrobacterium mediated transformation, by microinjection, by bombardmant with DNA-coated microparticles, by PEG mediated transformation, by electoporation and by other techniques known by those skilled in plant genetic engineering.

The CryIC δ-endotoxin, and transgenic plants which express this insecticide, may be employed to safeguard against all members of the Spodoptera species. Important Spodoptera pests include *S. exigua* (Beet armyworm), *S. litura* (Rice cutworm, Common cutworm), *S. maurita* (Paddy armyworm), *S. eridania* (Southern armyworm), *S. praefica* (Western yellow-striped armyworm), *S. ornithogalli* (Cotton cutworm), and others. The toxin according to the present invention is also believed to be effective against species of Mamestra genus, including *M. brassica* (Cabbage moth), *M. configurata* (Bertha armyworm), *M. illoba* (Mulberry Caterpiller), *M. persicariae* (Beet Caterpiller) and others. The effective CryIC $LC_{50}$ doses for *M. brassica* were reported at levels even 5 fold lower than those required for *S. littoralis* (Hofte, Whitely, 1989). *M. brassica* is a serious pest on many crops, mainly Brassica crops, totally polyphagous, abundant and widespread. *M. configurata* is an important economic pest on oil seed crops such as canola, *B. napus* and *B. rapae* in Canada and the United States.

Although CryIC δ-endotoxin is the most active *Bt* toxin against Spodoptera and Mamestra species, it has insecticidal activity towards other important pests of Lepidoptera order, such as *Trichoplasia ni* (Cabbage semilooper), *Plutella xylostella* (Diamondback moth), *Pieris brassica* (Large white butterfly), *Pieris rapae* (Small white butterfly) with the $LC_{50}$ doses, that are comparable or even lower of those required for protection against Spodoptera insects. Therefore, synthetic cryIC gene of present invention can be used not only as a monotransgene, but it can also be included in various strategies with multiple *Bt* genes in order to fight or to avoid an appearance of *Bt* resistant insect pests.

In addition to the activity towards Lepidoptera, the CryIC δ-endotoxin is toxic to the larvae of several dipteran insects, such as *Aedes aegypti, Anopheles gambia, Culex quinquefasciatus* (Smith et al., 1996). This fact opens a possibility to use the synthetic cryIC gene for creation of transgenic mammals in order to protect cattle and other suffering animals from dipteran vectors of various diseases as well as to protect livestock from irritating attacks of swarm of midges to increase, for example, milk or meat production.

*Bt* δ-endotoxins are accumulated in bacteria as insoluble inclusions, which upon ingestion by insect larvae must be activated by midgut proteases. Truncated *Bt* δ-protoxins are produced in *E. coli* as insoluble inclusion bodies, consisting of misfolded proteins, that in turn greatly reduces toxicity. However, the truncated CryIC produced in transgenic plants expressing the synthetic cryIC gene according to the present invention is highly soluble which renders it useful in a variety of industrial and agricultural applications. In transgenic Arabidopsis, containing the synthetic cryIC gene of the present invention, CryIC protein was accumulated up to 1% of total soluble protein, i.e., 25 ng per microliter in contrast to the solubility of the truncated CryIC produced in *E. coli* (0.8 ng per microliter). Whole amount of CryIC protein is deposited in a soluble fraction of the plant cell. The fact that the plant produced CryIC δ-endotoxin is soluble permits its use as a new product exploiting its solubility properties (e.g., a water based spray). The soluble CryIC protein produced by transgenic plants may be employed in insecticidal formulations either in an isolated form or with an agriculturally acceptable carrier that are well known to those skilled in insecticide formulation.

One disadvantage of microbial *Bt* formulations is a high price of the production requiring the marginally economic use of fermenters and media for bacterial growth. However, transgenic plants with synthetic cryIC according to the present invention, for example, alfalfa, are free from these limitations. Insect self-protected plant material can be collected during several years by cutting plants in fields. Due to its water solubility, the plant produced CryIC insecticide can be easily extracted from the collected plant material.

EXAMPLES

The following Examples are provided to illustrate the practice of the invention and are not intended to limit the scope thereof.

Example I—Gene Synthesis

Gene Construction

FIG. 2 shows the nucleotide sequence of the synthetic cryIC gene (SEQ ID NO:1) (s-cryIC). Nucleotides of the bacterial cryIC sequence (SEQ ID NO:3) (b-cryIC) exchanged in the synthetic gene are shown in the upper lanes. The nucleotide sequence of the s-cryIC coding region for 630 codons starts with an ATG codon in a sequence context fitting the eukaryotic consensus and terminates at a TAG stop codon. Arrowheads above the s-cryIC sequence indicate the boundaries of adjacent synthetic oligonucleotides used for TDL-PCR gene synthesis. HincII and BglII cleavage sites used for the assembly of three TDL-PCR blocks are indicated by boxes above the sequences. The amino acid sequence (SEQ ID NO:2) of the truncated CryIC δ-endotoxin is displayed in single letter code below the s-cryIC sequence.

Figure 1:
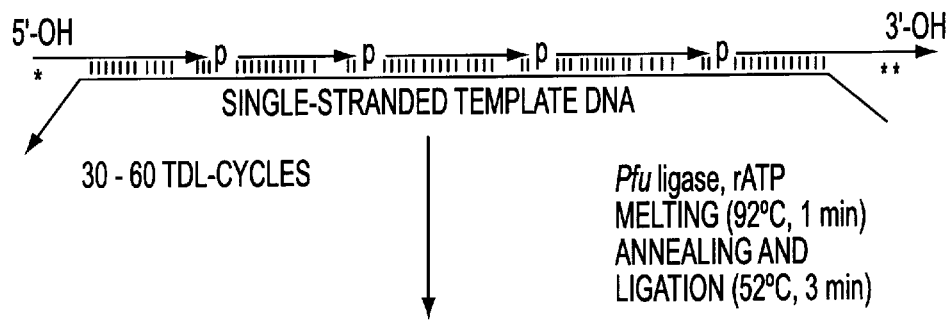
FIG. 1 is a schematic plan for the gene synthesis method according to the present invention.
Figure 1:
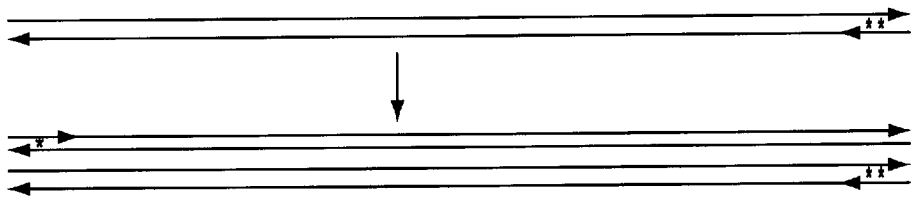

The designed DNA sequence of the s-cryIC gene (FIG. 2) was divided into three blocks separated by HincII and BglII cleavage sites. The BamHI-HincII block-I was constructed from eight, the HincII-BglII block-II from five, and the BglII-BamHI block-III from seven oligonucleotides. The oligonucleotides were assembled on a single-stranded DNA template of phagemid pR1, carrying the 630 N-terminal codons of the wild-type *B. thuringiensis* cryIC gene (FIG. 1 and 2). Terminal oligonucleotides in each TDL-PCR block carried unique sequences on their 5' and 3' ends, which were not complementary with the template, but were matched to short PCR primers for selective amplification of the synthetic DNA strand. These PCR primers contained unique restriction enzyme cleavage sites used for cloning of the amplified double-stranded DNA fragments into pBluescript. The TDL-PCR block-I was PCR amplified by a 5'-primer (SEQ ID NO:4) (5'-AAGAGGATCCACCATGGAGGAGAAC-3'), carrying a BamHI site and a 3'-primer (SEQ ID NO:5)(5'-ATGATCTAGATGCAGTA GCG-3'). The 3'-primer was complementary to an oligonucleotide (SEQ ID NO:6). (5'-GTCAACTAACAAGGGAAGTTTATACGGACCCAC-GCTACTGCATCTAGATCAT-3') at the 3'-end of block-I, that carried cryIC sequences with the HincII site, and unrelated overhang sequences with an XbaI site. The oligonucleotide at the 5'-end of block-II (SEQ ID NO:7) (5'-GATAACTCGAGCGAGCCTAAACTATGA-CAATAGGAGATACCAA TTCAGCCAGTTG-3') added unique DNA sequences with an XhoI site to the cryIC sequences upstream of the HincII site and matched a PCR primer (SEQ ID NO:8) (5'-GATAACTCGAGCGAGCCTA-3'). The 3'-terminal oligonucleotide in block-II carried cryIC sequences extending to the BglII site and downstream overhang sequences with an XbaI site that were complementary to a PCR primer (SEQ ID NO:9) (5'-CCTGACTCTAGAAG ATC-3'). In the oligonucleotide located at the 5'-end of block-III an EcoRI site was added upstream to the BglII site of cryIC gene, fitting to a PCR primer (SEQ ID NO:10) (5'-CTGTCTGAATTCAAAGATC-3'). The oligonucleotide at the 3'-end of block-III carried a BamHI site, following the position of TAG stop codon in the pR1 phagemid, as well as adjacent unique sequences with a NotI site that were complementary to a PCR primer (SEQ ID NO:11) (5'-AGCATGCGGCCGCGGATCC-3').

TDL Technique

Template directed ligation (TDL) reactions were carried out at a template to oligonucleotide ratio 1:200 (a total of 0.05 pM of template versus 10 pM of each oligonucleotide) in a final volume of 50 µl using a reaction buffer (20 mM Tris.HCl (pH 7.5), 20 mM KCl, 10 mM MgCl$_2$ 0.1% NP-40, 0.5 mM rATP, 1 mM DTT)-and 4 U Pfu DNA ligase (Stratagene), or any other similar thermostable DNA ligase.

Thirty cycles of TDL reactions were used to obtain a desirable amount of a TDL product. The temperature range during melting step is between 90 to 98° C. with a preferable temperature of 92°, with 1 minute of required step time. Annealing and ligation were performed at a temperature range of 45 to 60° C. with a preferable temperature of 52° C. during required step time from 3 to 10 minutes. Melting step was followed by annealing and ligation step to obtain a TDL cycle which was repeated at least 30 times. To increase the number of TDL cycles for every additional 30 cycles a new portion of rATP (0.5 mM) and 4 U of Pfu ligase was added. Temperature cycling during TDL step was done on a Perkin-Elmer thermal cycler (Norwalk, Conn.).

PCR Selective Amplification of Synthetic TDL-PCR Blocks

5 µl from the TDL reaction mix served as template for PCR amplification with 100 pM of primers, 250 µM dNTP and 2.5 U Ampli-Taq or any other similar thermostable DNA polymerase such as UlTma (Perkin-Elmer) polymerase in 100 µl buffer (10 mM Tris.HCl (pH 9.0), 50 mM KCl and 0.1% Triton-X100), using 30 cycles at 92° C. for 1 min, 45° C. for 1 min, and at 72° C. for 1.5 minutes, with final extension for 10 minutes, at 72° C. PCR amplifications were performed on a Perkin-Elmer (Norwalk, Conn.) thermo cycler. The amplified DNA fragments were gel purified, digested with BamHI-XbaI (block-I), XhoI-XbaI (block-II), and EcoRI-NotI (block-III), then cloned in pBluescript SK+ to verify their DNA sequences.

Design of Synthetic cryIC Gene Aimed to be Transferred to Plants a) Identification of the minimal entomocidal fragment of Spodoptera specific Bt toxin CryIC. From prior art it is known that expression of the truncated Bt genes in transgenic plants was superior compared to the full-length genes of protoxins. Moreover, identification of the minimal toxic fragment of a protoxin would significantly reduce efforts and costs involved in construction of a synthetic gene. In CryIA proteins the tryptic fragment, which is still responsible for toxicity, composes a half of the protoxin. To improve the production of recombinant CryIC toxins, we mapped the minimal toxic fragment of the protoxin by testing of various truncated proteins for the stability and protease sensitivity to trypsin and Spodoptera midgut proteases as well as by the measurement of the insecticidal activity to S. littoralis larvae. In contrast to previous data, the boundaries of trypsin-resistant CryIC core toxin were mapped to amino acid residues 128 and R627. Proteolysis of the truncated CryIC proteins showed that Spodoptera midgut proteases may further shorten the C-terminus of CryIC toxin to residue A615. However, C-terminal truncation of CryIC to residue L614, and a mutation causing amino acid replacement I610T abolished the insecticidal activity of CryIC toxin to S. littoralis larvae, as well as its resistance to trypsin and Spodoptera midgut proteases. Because no CryIC toxin carrying a proteolytically processed N-terminus could be stably expressed in bacteria, our data indicate that in contrast to other CryI proteins an entomocidal fragment located between amino acid positions 1 and 627 is required for stable production of recombinant CryIC toxins.

b) Establishment of the CryICa5 protein sequence. Design of the synthetic cryIC gene was based on the sequence of the corresponding wild-type gene (cry1Ca5, EMBL X96682), which we established after sequencing of three independent cryIC genes isolated from three different B. thuringiensis strains K26-21, MR1-37 (new isolates, collected from the soil samples in Kenya and Israel, respectively) and subsp. aizawai 7.29, all selected for high insecticidal activity against larvae of the S. littoralis. We have found that all the three strains contain the identical cryIC gene sequence, which has certain discrepancies with all the cryIC sequences known in prior art (cry1Ca1—Honee et al., 1988; cry1Ca2—Sanchis et al., 1989; cry1Ca3—U.S. Pat. No. 5,246,852, 1993; cry1Ca4—EP 0400246, 1995). Moreover, in fact, the cry1Ca5 sequence represents a consensus of all known cryIC genes.

Corresponding sequence of Cry1Ca5 protein differs by amino acid replacements A124E, A294R, and H453D from the Cry1Ca1, by a T405Q exchanges from the Cry1Ca3, and by the A124E from the CryICa4. Similarly, multiple sequence shifts resulting in N366I, V386G and 376WPAP-PFN382 (SEQ ID NO:13) to 376CQRHHFN382 (SEQ ID NO:14) amino acid replacements were found in the previously published cryIC sequence from subsp. aizawai 7.29 (Sanchis et al, 1989). The occurrence of glutamate in position 124 and glutamine in position 405 were clearly due to previous errors, since A124 and T405 were found to be conserved in all CryIC proteins. Similarly, sequence variations detected between positions 366 and 386 of the CryIC sequence from subsp. aizawai 7.29 could safely be excluded because they would either create a new tryptic cleavage site, such as the R378 residue, or affect the activity and insect specificity of the toxin, such as the W376C replacement and the 374QPWP377 (SEQ ID NO:15) motive that are located in a surface exposed loop of the variable toxin domain II. Therefore, we believe that the CryIC sequences, known in prior art, contain critical errors with negative consequences either for function or stability of CryIC protein, had the protein a corresponding synthetic gene designed on the basis of the wild-type DNA sequences known in prior art. Modifications of the synthetic cryIC gene (s-cryIC) sequence of the present invention did not alter the amino acid sequence of the minimal toxic fragment of the Cry1Ca5 protoxin, containing N-terminal fragment with the length of 630 amino acid residues.

The synthetic cryIC gene coding for an N-terminal protoxin fragment of 630 amino acids was designed (FIG. 2) by exchanging 286 bp of the bacterial cryIC sequence (EMBL X96682; 1890 bp) such that 249 out of 630 codons were modified according to preferential codon usage in dicotyledonous plants. These exchanges removed 21 potential plant polyadenylation signals, 12 ATTTA motifs, 68 sequence blocks with 6 or more consecutive A/T's, and all motifs containing 5 or more G+C or A+T nucleotides. Sequences around the translation initiation site were changed to conform to the eukaryotic consensus sequence, and a TAG stop codon was introduced downstream of amino acid codon 630. The G+C content of the cryIC gene was thus increased from 36.6% to 44.8%. The s-cryIC gene was synthesized from oligonucleotides of 70–130 bases that were chemically phosphorylated at their 5'-ends. Since chemical phosphorylation is performed as the last step of automated DNA synthesis, only full-length oligonucleotides contain the 5'-phosphate group. Bacterial cryIC sequences coding for the 630 N-terminal codons were cloned in a pBluescript vector to generate a single-stranded DNA template for ordered annealing of 5–8 synthetic oligonucleotides by partial base-pairing. The adjacent oligonucleotides were assembled and ligated on this single-stranded template by a thermostable Pfu-ligase using 30–60 cycles of repeated melting, annealing and ligation. In combination with chemical phosphorylation this template directed ligation (TDL, FIG. 1) method provided a sequence specific selection for phosphorylated full-length oligonucleotides from a complex mixture of nonphosphorylated failure synthesis products, and yielded a linear amplification of single-stranded synthetic cryIC DNA segments generated by ligation. Therefore, except for desalting, no additional purifications of a crude oligonucleotide mixture after chemical DNA synthesis were necessary. The TDL ligation at high temperatures also circumvented potential problems of erroneous annealing. The synthetic cryIC sequences were converted to double-stranded DNA fragments and specifically amplified by PCR using short end-primers that did not anneal to the bacterial cryIC template carried by the pBluescript vector. The s-cryIC gene was thus synthesized from three sequence blocks that were combined by ligation of HincII and BglII digested DNA fragments, and cloned in pBluescript.

With further reference to the Figures relating to this Example, FIG. 2 shows the nucleotide sequence of the synthetic cryIC gene (s-cryIC). Nucleotides of the bacterial cryIC sequence (b-cryIC) exchanged in the synthetic gene are shown in the upper lanes. The nucleotide sequence of the s-cryIC region coding for 630 codons starts with an ATG codon in a sequence context fitting the eukaryotic consensus and terminates at a TAG stop codon. Vertical black arrows above the s-cryIC sequence indicate the boundaries of adjacent synthetic oligonucleotides used for TDL-PCR gene synthesis. HincII and BglII cleavage sites used for the assembly of three TDL-PCR blocks are framed.

TABLE I

Summary of Changes Introduced in the Truncated Synthetic cryIC Gene (s-cryIC) Compared to the Natural Counterpart (n-cryIC)

|  | s-cryIC | n-cryIC |
| --- | --- | --- |
| G + C content | 44.8% (exon like) | 36.6% (intron like) |
| Bases different from wild type | 285 of 1890 (15.1%) | — |
| Codons different from wild type | 249 of 630 (39.4%) | — |
| Potential plant polyadenylation sequences (Dean et at., 1986) | — | 21 |
| ATTTA sequences | — | 12 |
| A + T - rich regions (>6 consecutive A and/or T) | — | 68 |

All codons rarely used in plants and present in the wild type cryIC were substituted by the most preferred codons in alfalfa and dicots plants.
G + C runs of 5 or more and A + T runs of 5 or more were avoided in the synthetic cryIC.
The sequence upstream of the translation initiation site was changed according to the eukaryotic consensus sequences.

Example II

Plant Gene Expression Constructs and Transformation of Alfalfa and Tobacco

The plant expression vector pPCV91 was constructed by modification of pPCV720. A NotI site in the RK2-domain was eliminated by filling in with DNA polymerase Klenow fragment, and a CaMV35S promoter with four repeats of the enhancer domain (−90 to −418), was introduced into the HindIII site of pPCV720. Upstream of a BamHI cloning site this cassette contained 20 bp from the 3'-end of the untranslated Ω leader sequence of tobacco mosaic virus (TMV) RNA, whereas downstream of the BamHI site it carried a polyadenylation signal sequence derived from the CaMV 35S RNA gene. A BamHI site present in the mannopine synthase dual promoter (pmas) of pPCV720 was replaced by a NotI site using a Sau3A-NotI adaptor (SEQ ID NO:12) (5'-GATCTGCGGCCGCA-3'). The resulting vector pPCV91 carried three plant gene expression cassettes with unique BamHI, NotI and SalI cloning sites. To construct pNS6, the synthetic cryIC gene was cloned as a BamHI fragment downstream of the CaMV35S promoter. In pNS7, a synthetic pat gene, encoding phosphinothricine acetyltransferase, and a chiAII gene from *Serratia marcescens* were inserted into the SalI and NotI sites located respectively downstream of the mas 1' and 2' promoters. In pAR1, the bacterial signal peptide of chiAII was substituted by the plant leader peptide derived from potato proteinase inhibitor. A bacterial cryIC gene from *B. thuringinesis* subsp. aizawai 7.29 (EMBL X96682), carrying the 756 N-terminal codons of cryIC, was cloned in pGIF1 in which it replaced the synthetic cryIC gene of pNS7. Vectors pNS6, pNS7, pGIF1 and pAR1 were conjugated to *Agrobacterium tumefacines* GV3101(pMP9ORK), and used for transformation of alfalfa (*Medicago sativa* L. var. Regen S clone RA3) and tobacco (*Nicotaina tabacum* SR1) and potato (*Solanum tuberosum* var. Desiree) as described (D'Halluin et al., 1990; Koncz et al., 1994). To select for transformed explant, alfalfa, tobacco, and potato tissue culture media contained 40 μg/ml for alfalfa and 15 μg/ml of hygromycin for the last two were used.

Seeds of tobacco transformed according to the procedure set forth herein were deposited as patent deposits on Dec. 23, 1996, under the Budapest Treaty on the International Recognition of the Deposit of Microorganisms for Patent Purposes at the American Type Culture Collection (ATCC), 12301 Parklawn Drive, Rockville, Md. under Accession Number ATCC 97837.

EXAMPLE III

Monitoring the Expression of CryIC in Transgenic Plants

Bacterial and synthetic cryIC genes, coding for the 630 N-terminal amino acids of the CryIC toxin (FIG. 2), were cloned into the BamHI site of a pAEN4 vector carrying the CaMV35S gene expression cassette of pPCV91. *Arabidopsis thaliana* protoplast were isolated from root cultures and transformed by PEG-mediated DNA uptake, using $1.5\times10^6$ protoplast and 35 μg plasmid DNA in each experiment. The protoplast were harvested 48 hours after DNA uptake and lysed in SDS-sample buffer to separate proteins on 10% SDS-PAGE before immunoblotting. A polyclonal antibody used for immunoblotting was raised against a truncated CryIC δ-endotoxin carrying 756 N-terminal amino acids. Expression of CryIC in *E. coli* strains, carrying bacterial or synthetic cryIC genes respectively in pET-11a or 11d, was monitored-by a second alkaline phosphatase conjugated goat anti-rabbit antibody. Immunoblott analysis of proteins synthesized in plant cells was performed using an ECL kit (Amersham).

RNA (20 μg) samples isolated from leaves and petioles of alfalfa plants were separated on agarose-formaldehyde gels.

BamHI fragments (1.9 kb), carrying either with synthetic or bacterial CryIC sequences (FIG. 2), and a NotI fragment with the chiAII gene (1.8 kb) were labeled by random-priming and used as hybridization probes. Similarly, RNA (20 µg) extracted from transgenic potato plants transformed with pAR1 was also subjected to Northern analysis, using separately s-cryIC as well as rDNA sequence as a specific and general probe respectively.

EXAMPLE IV

Insect Bioassay

Leaf bioassay were performed with the Egyptian cotton leafworm (*Spodoptera littoralis*) and the beet armyworm (*Spodoptera exigua*) using neonate, 2–3rd, 3–4th, and 4–5–6th instar larvae. Ten larvae of a selected developmental stage were placed on a moistened filter disc in Petri dishes with detached leaves from greenhouse grown plants. The assays were repeated 2–3 times for each plant. The mortality of neonate larvae was scored after 3 days, whereas the mortality of larvae from 2–4th and from 4–6th instar stages were evaluated respectively after 5 and 7 days. For the insect assays with whole plants, transgenic greenhouse grown alfalfa lines producing 0.02 to 0.1% of total soluble protein as CryIC and *S. exigua* larvae of the 3–4th instar stage were used. Three NS7 and three NS6 transgenic, as well as wild-type plants were infested with 15–20 larvae each. In "free-choice" experiments, 25 larvae were placed in a Petri dish located between transgenic NS6 or NS7 and nontransgenic alfalfa plants in the greenhouse. Leaf damage was evaluated after 6 days.

Potato leaves expressing about 0.02–0.05% of their total proteins as CryIC were assayed for their toxicity to *S. littoralis*. Only a single primary transformant out of 10 was less resistant to Instar III and IV larvae. This plant was later shown to contain at least 8 copies of s-cryIC that probably co-suppress each other.

EXAMPLE V

Expression of cryIC Genes in *E. coli*, Arabidopsis, Alfalfa, Tobacco, and Potato FIG. 3 (A) comprises a schematic map of plant transformation vectors. The synthetic s-cryIC gene is cloned in an optimized gene expression cassette in pNS6 between pro-motor (pCaMV35S) and polyadenylation sequences (pA35S) from the 35S RNA gene in Cauliflower Mosaic Virus. The CaMV35S promotor contains 4 repeats of the upstream enhancer region (−90 to −418) marked by open boxes. The same CaMV35S expression cassette is carried by a pAEN4, a vector used for transient expression of bacterial b-cryIC and synthetic s-cryIC genes in Arabidopsis protoplasts. In addition to cryIC, vector pNS7 contains a phosphinothricine acetyltransferase gene (pat) under the control of mannopine synthase (mas) 1'-promoter, and chitinase AII (chiAII) gene driven by the mas 2' promoter. The chiAII has a plant leader peptide instead of the native bacterial sequence of the original chiAII in pAR1, the rest of the plasmid sequence is similar to pNS7. pAR1 was introduced into potato and tobacco using *Agrobacterium tumnefaciens* GV3101, pMP90RK. The s-cryIC gene of pNS7 was exchanged for the bacterial b-cryIC gene in pGIF1. The structure of pGIF1 is otherwise identical with that of pNS7. Abbreviations: $ori_T$ and $ori_V$, conjugational transfer and vegetative replication origins of plasmid RK2; LB and RB, the left and right 25 bp border repeats of the T-DNA, respectively; $ori_{pBR}$, replication origin of pBR322; $AP^R$, bacterial ampicillin resistance gene; pg5, promoter of gene 5; pnos, nopaline synthase promoter; hpt, hygromycin phosphotransferase gene; pA4 and pA7, polyadenylation signal sequences of the T-DNA encoded genes 4 and 7, respectively; $pA_{OCS}$, polyadenylation signal sequence of the octopine synthase gene. Open arrows label plant promoters, black boxes mark plant polyadenylation signal sequences.

Figure 3A:
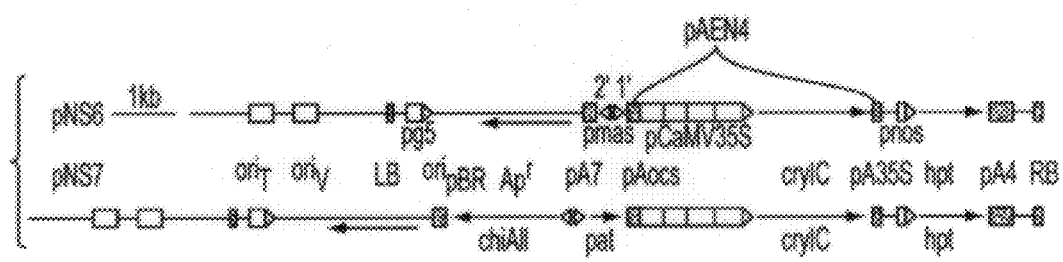
FIG. 3A is a schematic map of plant transformation vectors.
Figure 3B:
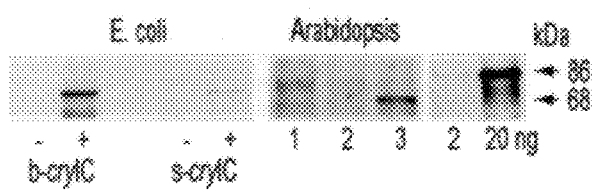
FIG. 3B is a photograph of Western blots showing expression of b-cryIC and s-cryIC genes in E. coli and Arabidopsis.

FIG. 3(B) relates to expression of b-cryIC and s-cryIC genes in *E. coli* and Arabidopsis. Left: The bacterial b-cryIC and synthetic s-cryIC genes were cloned respectively in vectors pET-11a and 11d, and their expression in *E. coli* was monitored with (+) or without (−) IPTG (isopropyl-β-thiogalactopyranoside) induction by immunoblotting, using a polyclonal anti-CryIC antibody. The lanes contain equal amounts of protein samples (15 µg) from *E. coli* extracts separated by SDS-PAGE. Right: Arabidopsis protoplasts were transformed by PEG-mediated DNA uptake with pAEN4 (1), and pAEN4-derived vectors carrying the b-cryIC (2) and s-cryIC (3) genes. Following transient expression for 48 hrs. 25 µg of soluble protein extracts prepared from protoplasts were separated by SDS-PAGE and subjected to immunoblotting. To estimate the amount of CryIC toxin in plant samples, purified CryIC protein of 86 kDa (carrying amino acid residues 1 to 756) was used as standard (2 and 20 ng.).

Figure 3C:
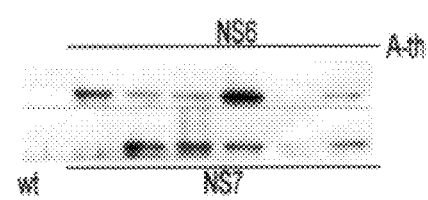
FIG. 3C is a photograph of Western blots showing screening for cryIC expression in alfalfa.

FIG. 3(C) relates to screening for CryIC expression in alfalfa calli, carrying the T-DNA of plant transformation vectors pNS6 and pNS7. Each lane contains 25 µg of soluble proteins from calli. For comparison, Arabidopsis protoplast extract (A.th), shown in lane 3 of (B), was loaded as standard, in addition to control protein extracts prepared from callus tissues of wild type (wt) nontransformed alfalfa.

Figure 3D:
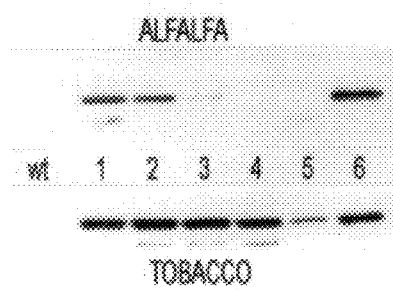
FIG. 3D is a photograph of Western blots showing screening for CryIC accumulation in leaf tissue of transgenic alfalfa and tobacco plants.

FIG. 3(D) Screening for CryIC accumulation in leaf tissues of transgenic alfalfa and tobacco plants. Soluble proteins (50 µg) were prepared from NS6 (lanes 1 and 3–6) and NS7 (lane 2) alfalfa transformants, as well as from transgenic tobaccos carrying the NS7 s-cryIC gene construct (bottom lanes 1–6).

Figure 3E:
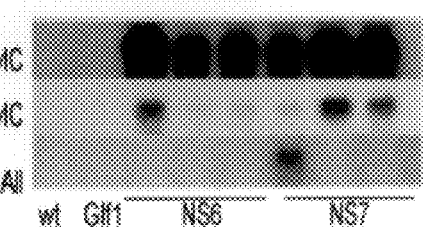
FIG. 3E is a photograph of a Northern blot showing screening for transcripts of transgenes in leaves of soil-grown alfalfa plants.

FIG. 3(E) Screening for transcripts of transgenes in leaves of soil-grown alfalfa plants carrying the T-DNA of pGIFI, pNS6 and pNS7 vectors (three lanes each for NS6 and NS7 reflect three independent transgenic plants). Each lane in the three identical blots contains 20 µg total RNA. The blots were hybridized respectively with s-cryIC, b-cryIC and chiAII probes labeled to similar specific activity. Although several GIFI transgenic plants expressing the chiAII gene were found during this screening (data not shown), no expression of the b-cryIC gene was detected in any GIFI transformant. (The positive hybridizations with the b-cryIC' probe are due to the partial homology between the synthetic and natural cryIC genes and the difference in the intensity of hybridizations with the s-cryIC and b-cryIC probes reflects differences between these cryIC sequences.)

Figure 3F:
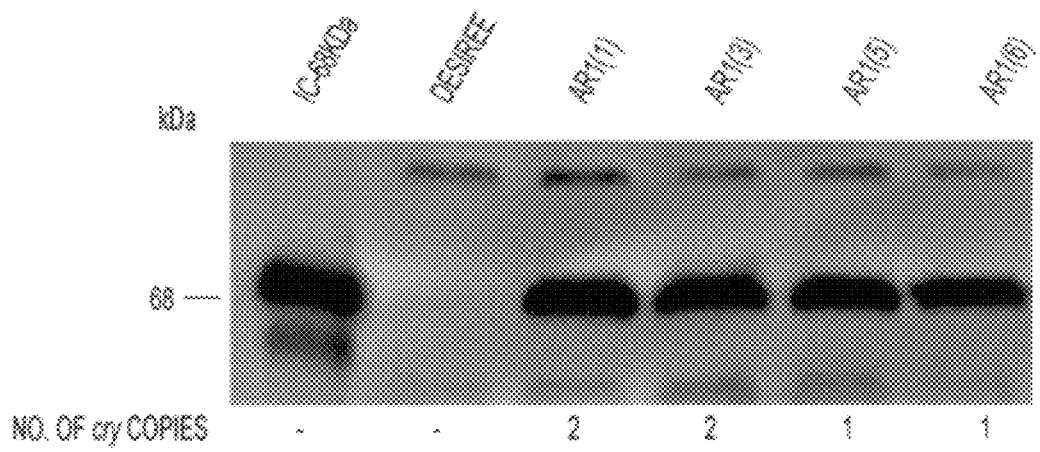
FIG. 3F is a Western blot analysis of leaf protein extracts from transgenic potato plants expressing the cryIC gene. 10 ng of truncated CryIC produced in E. coli (positive control), total proteins (50 µg) from plant var. Desiree (negative control) and transformed plant number 1,3,5 and 6 containing 2,2,1 and 1 copies of the cryIC gene respectively, were electrophoresed on 12% polyacrylamide gels, then transferred to PVDF membrane. The blot was incubated with rabbit-anti CryIC, and then with horseradish peroxidase conjugated to anti-rabbit immunoglobulin. Enzymatic visualization of immunoreactive CryIC was then carried out.

FIG. 3F is a Western blot of total proteins (50 µg/lane) extracted from leaves of transgenic potato plants transformed with pAR1 and probed with anti-CryIC polyclonal antibodies. The left lane contains 10 ng *E. coli*-produced CryIC (first 630 amino acids). CryIC constituted for about 0.02 to 0.05% of the total leaf proteins.

Figure 3G:
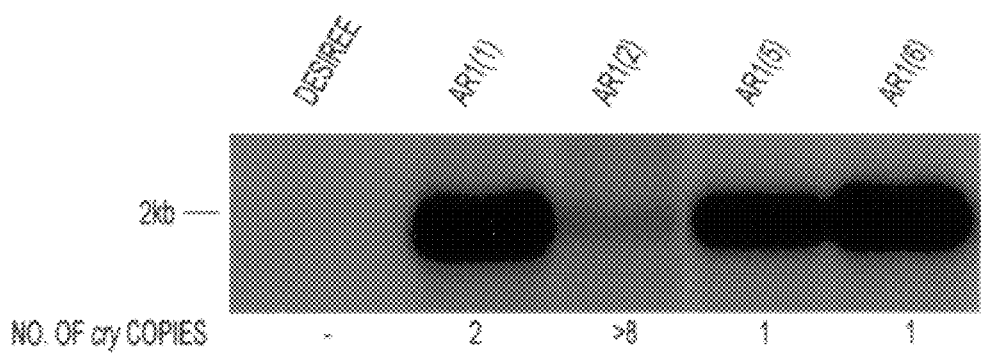
FIG. 3G is a Northern blot analysis of cryIC gene transcripts in transgenic potato plants. Total RNA (15 µg) extracted from untransformed Desiree plant and transgenic plants AR1(1, 2,5 and 6) resulted from transformation with the binary vector pAR1, were electrophoresed with glyoxal in 1% agarose TBE gels, then transferred onto nylon membrane and probed with $^{32}$P labeled cryIC gene. The number of introduced cry copies per plant is indicated below.

FIG. 3G is a Northern blot analysis of leaf RNA (16 µg) extracted from transgenic potato plants and probed with the coding region of s-cryIC (shown in FIG. 3G) and then with rDNA probe to evaluate the total RNA amount loaded on each lane. Transgenic plants AR1-5, AR1-6, AR1-7, and AR1-8 revealed equal levels of s-cryIC transcripts while 2 fold higher level was found in AR1-1 and 1/1-level in AR1-2 that also revealed less production of CryIC and low resistance to the larvae.

Bacterial and synthetic cryIC genes were cloned respectively in vectors pET-11a and 11d, and expressed in *E. coli*. The synthesis of CryIC protein was monitored by immunoblotting. In comparison to cells harboring the bacterial cryIC gene, the expression of the synthetic gene in *E. coli* yielded a significantly lower toxin level (FIG. 3B).

The native and synthetic cryIC genes were inserted between promoter and polyadenylation signal sequences of the Cauliflower Mosaic Virus (CaMV) 35S RNA gene in the plant gene vector pAEN4. In pAEN4 the 5'-ends of cryIC genes were fused to untranslated Ω leader sequences of the Tobacco Mosaic Virus (TMV) to enhance the translation of mRNAs, whereas the upstream CaMV 35S promoter was supplemented with 4 repeats of the enhancer domain (−90 to −418), to stimulate the transcription of chimeric genes in plants. The cryIC genes were introduced by PEG-meditated transformation into Arabidopsis protoplasts, and the accumulation of CryIC toxin was monitored by immunoblotting following transient gene expression (FIG. 3B). In protoplasts carrying the bacterial gene no toxin was detectable, whereas cells transformed with the synthetic gene accumulated significant amount of CryIC protein (FIG. 3B).

The cryIC genes were transferred into pPCV91, a T-DNA-based transformation vector carrying a selectable hygromycin resistance (hpt) gene. In the dual gene expression cassette of pPCV91 (FIG. 3A), a synthetic phosphinothricine acetyltransferase (pat) gene was cloned downstream of the mannopine synthase (mas) 1' promoter, to link the cryIC genes to a genetic marker allowing field-selection of transgenic plants by the herbicide BASTA. A chitinase AII (chiAII) gene from *Serratia marcescens* was inserted downstream of the mas 2' promoter, because our previous studies indicated that chitinases may enhance the insecticidal activity of *Bt* toxins by destroying the chitinous peritrophic membrane of insect midgut. The pPCV91 constructs, carrying the native, or synthetic, cryIC genes either alone, or in combination with a pat and chiAII genes, were introduced by Agrobacterium-mediated transformation into alfalfa, tobacco, and potato. From tobacco and potato calli and somatic embryos of alfalfa selected on hygromycin, transformed shoots were regenerated. Transgenic plants derived from each transformation were assayed for the synthesis of CryIC toxin in leaves by immunoblotting, and for cryIC gene expression using RNA hybridization. In calli or in plants carrying the bacterial cryIC gene (confirmed by DNA hybridization, data not shown), neither stable steady-state cryIC mRNA (FIG. 3E) nor toxin could be detected (data not shown). In contrast, transformed calli (FIG. 3C) as well as shoots carrying the synthetic gene (FIG. 3D), synthesized the CryIC toxin and accumulated significant amounts of steady-state cryIC mRNA (FIG. 3E). Shoots producing detectable amounts of CryIC toxin (0.01–0.2% of soluble leaf proteins) were vegetatively propagated and, if they carried the pat and chiAII genes, were further exposed to BASTA selection in the greenhouse and tested by RNA hybridization (FIG. 3E) using the corresponding genes as probes.

EXAMPLE VI

Figure 4A:
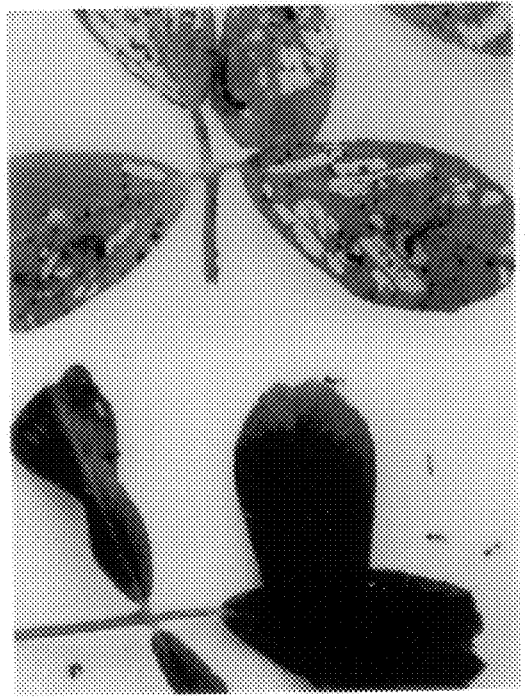
FIGS. 4A–4E is a photograph showing screening for Spodoptera resistance in transgenic plants.
Figure 4C:
Figure 4D:

Assaying Resistance of cryIC Transgenic Plants to the Egyptian Cotton Leafworm and Beet Armyworm Transgenic alfalfa plants obtained by transformation with the pNS6 and pNS7 constructs (FIG. 3A) were tested for insect tolerance by feeding leaves to neonate larvae of the Egyptian cotton leaf worm (*S. littoralis*). 15 out of 27 NS6 transformants, and 14 out of 32 NS7 transformants produced 100% mortality of larvae (FIG. 4A, Table 2). Immunoblotting of leaf protein extracts showed that these plants produced 0.01–0.1% of total soluble protein as CryIC toxin in leaves (FIG. 3D). Leaves from these plants used in the diet of beet armyworm (*S. exigua*) also caused 100% mortality of larvae throughout their development (FIG. 4C–D), Table 2). Screening of the NS7 transgenic alfalfa demonstrated that 15 out of 32 tested plants (47%) exhibited the high level CryIC production (0.02–0.1% of total soluble protein), 2 plants (6%) had low toxin levels (less than 0.02%) and in 15 plants (47%) CryIC levels were below the detection limit of immunoblotting with 50 mg of soluble protein. NS6 transgenics consisted of 5/15 (33%) of high level, 7/15 (47%) low level, and 3/15 (20%) undetectable CryIC expressors.

About 80 hygromycin resistant potato plants (cultivars Desiree) were regenerated and 9 of them were subjected to molecular analysis and bioassays. Two out of 9 plants did not express CryIC and were sensitive to *S. littoralis* larvae. The rest of the 7 plants displayed resistance to all instar larvae. While the plant AR1-2 was less resistant, the other 6 plants were totally resistant to all instar larvae and contain 1-3 inserted copies of s-cryIC (FIG. 3(F). At least eight copies of s-cryIC were detected in the plant AR1-2. The potato-produced CryIC was less susceptible to proteolysis by the *S. littoralis* gut proteases (FIG. 7), but denaturation and renaturation in vitro render it susceptible to proteolysis.

From 63 NS7 tobacco transformants 42 lines (66.6%) were resistant to 1.0% BASTA, Proper Mendelian segregation of a BASTA and hygromycin resistance markers was confirmed after selfing 11 transgenic tobacco lines. From these BASTA resistant plants 10 stocks were assayed by immunoblotting and found to produce 0.1–0.2% of leaf soluble proteins as CryIC toxin (FIG. 3D) and resulted in 100% mortality of *S. exigua* larvae. 3 from these lines were used in bioassays with *S. exigua* and found to cause 100% mortality of larvae from different developmental stage.

The insecticidal assays showed no difference between plants carrying the cryIC gene alone or in combination with the chiAII gene. A synergistic effect between chitinase AII and CryIC toxin could have escaped our detection because toxin levels as low as 0.01% of total plants were sufficient to kill all larvae. To imitate field conditions, CryIC expressing plants were infested by 15–20 larvae of 3rd–4th instar stage in the greenhouse. After 6 days, no viable insect escapes were detected and the transgenic plants suffered barely detectable leaf damage; on average less than 1% of the leaf area was affected. Infestation of a mixed population of wild-type and transgenic plants carrying the synthetic cryIC gene resulted in devastation of wild-type, but yielded no apparent colonization of worms on the CryIC toxin expressing plants in the population. Similar results were obtained by infesting detached leaves from these plants with larvae of *S. exigua*.

EXAMPLE VII

Screening for Spodoptera Resistance of Transgenic Plants

FIG. 4(A) shows an insecticidal assay with neonate larvae of *S. littoralis* reared for 2 days on leaves from non-transformed alfalfa (*M. sativa*, top) and NS7 transgenic (bottom) plants.

Figure 4B:
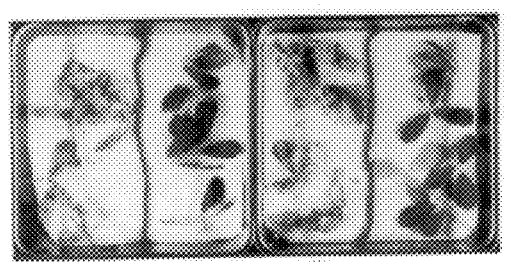

FIG. 4(B) shows "free choice" bioassays with leaves from wild-type and transgenic alfalfa plants. In the plate to the left 10 larvae of *S. exigua* (3rd instar) were placed on the red line located between leaves of wild-type (left) and NS7 transgenic (right) alfalfa plants. In the plate to the right, the larvae were placed between leaves from wild-type (left) and NS6 (right, FIG. 3D, lane 6) transgenic alfalfas. For 5 days the larvae failed to colonize leaves from the transgenic plants in both assays.

FIG. 4(C–D) shows leaves from tobacco (C) and alfalfa (D) plants were used for feeding of five fifth instar larvae of *S. exigua* for 10 hrs. Petri dishes to the left in (C–D) contained leaves from nontransformed plants. Leaves shown in Petri dishes to the right in (C–D) were collected from a NS7 tobacco transgenic line producing 0.2% of soluble proteins as CryIC toxin (FIG. 3D, lane 2), and from a NS6 alfalfa transformant producing 0.1% of leaf proteins as CryIC toxin, respectively.

Figure 4E:

FIG. 4(E) shows transgenic NS7 (left, FIG. 3D, lane 2) and nontransformed alfalfa (right) plants were infested with 15 larvae of *S. exigua* (3–4th instar stage) for 6 days.

FIG. 5 demonstrates the resistance of transgenic potato leaves resulted from pAR1 introduction to 2nd, 3rd and 4th instar larvae of *S. littoralis*. Leaves of plant AR1-2 less resistant while the control leaves were partially or totally consumed by the young and older larvae respectively. The leaves were photographed after 24 h of exposure to the larvae.

FIG. 6 is a Southern analysis of transgenic potato plants showing the integration of 1 to at least 8 copies of cryIC. The plant number is indicated above the lanes, probes-below the panels.

FIG. 7 is a Western blot performed with total proteins extracted from transgenic potato leaves or from *E. coli* expressing the 630aa CryIC, and incubated for 2, 10, 20 min. with gut juice of the 4th instar larvae of *S. littoralis*. The *E. coli* produced CryIC is more susceptible to proteolysis. Denaturation of the plant CryIC abolishes its resistance to proteolysis.

The control of Spodoptera (armyworms) by transgenic alfalfa plants shown in Table 2.

TABLE 2

| | Mortality of *S. littoralis* neonate larvae | | |
|---|---|---|---|
| | 95–100% | 30–90% | <30% |
| NS6 | 15/27 *(55.5%) | 5/27 (18.5%) | 7/27 (33.3%) |
| NS7 | 14/32 (43.8%) | 5/32 (15.6%) | 13/32 (40.6%) |

| Mortality of *S. exigua* larvae fed on leaves of plants With 0.02–0.1% CryIC toxin level | | | |
|---|---|---|---|
| Transgenics | NS6 (number of | NS7 plants tested) | Time of scoring (days) |
| Instar 1 | 100% (1) | 100% (3) | 3 |
| 2–3 | 100% (5) | 100% (7) | 5 |
| 3–4 | 100% (2) | 100% (3) | 5 |
| 4–5–6 | 100% (3) | 100% (2) | 7 |

*The figures show the ratio between the numbers exhibiting the corresponding mortality rate to the total number of transgenic plants tested; in parenthesis this fraction in %.

Out of 60 NS7 transgenic alfalfa plants 14 lines were found to be resistant to 0.1–0.2% BASTA. From these plants 9 lines displayed high levels (0.02–0.1%) of CryIC toxin production in leaves and caused 100% mortality of both *S. littoralis* and *S. exigua* larvae.

Although only preferred embodiments are specifically described herein, it will be appreciated that many modifications and variations of the present invention are possible in light of the above teachings and within the purview of the appended claims without departing from the spirit and intended scope of the invention.

What is claimed is:

1. An isolated DNA sequence coding for a *Bacillus thuringiensis* CryIC protein comprising the nucleotide sequence shown in SEQ ID NO: 1.

2. The isolated DNA sequence of claim 1 wherein said nucleotide sequence codes for a *Bacillus thuringiensis* CryIC toxin between amino acid 1 and amino acids 615 and 630 as shown in SEQ ID NO: 2.

3. A vector comprising the isolated DNA sequence of claim 1.

4. A transformed plant cell comprising the isolated DNA sequence of claim 1.

5. A transgenic plant comprising the isolated DNA sequence of claim 1.

6. The transgenic plant of claim 5, wherein said plant is selected from the group consisting of potato, tomato, tobacco, cotton, sunflower corn and alfalfa.

7. The transgenic plant of claim 6, wherein said plant is a tobacco plant produced from seeds having ATCC deposit accession No. 97837.

8. A method of increasing plant resistance to an insect pest comprising the steps of:
  (a) transforming a plant cell with an isolated DNA sequence coding for a *Bacillus thuringiensis* CryIC protein comprising the nucleotide sequence shown in SEQ ID NO: 1; and
  (b) regenerating a fertile transgenic plant from said transformed plant cell which expresses said CryIC protein.

9. The method of claim 8, wherein said nucleotide sequence codes for a *Bacillus thuringiensis* CryIC toxin between amino acid 1 and amino acids 615 and 630 as shown in SEQ ID NO: 2.

10. The method of claim 8, wherein said transgenic plant is selected from the group consisting of potato, tomato, tobacco, cotton, sunflower, alfalfa, rice, and corn.

11. The method of claim 8, wherein said insect pest is in a genus selected from the group consisting of Spodoptera, Mamestra, Phtorimea, Trichoplusia, Plutella, Pieris, Chilo and Sciropophage.

* * * * *